US012611275B2

(12) United States Patent
Adams et al.

(10) Patent No.: US 12,611,275 B2
(45) Date of Patent: Apr. 28, 2026

(54) MANUAL END EFFECTOR ACTIVATION FOR ROBOTIC SURGICAL SYSTEMS

(71) Applicant: Covidien LP, Mansfield, MA (US)

(72) Inventors: Crystal A. Adams, Westminster, CO (US); Zachary S. Heiliger, Nederland, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/441,762

(22) Filed: Feb. 14, 2024

(65) Prior Publication Data

US 2024/0180657 A1      Jun. 6, 2024

Related U.S. Application Data

(63) Continuation of application No. 16/988,122, filed on Aug. 7, 2020, now Pat. No. 11,925,428.

(51) Int. Cl.
    *A61B 17/00*     (2006.01)
    *A61B 34/00*     (2016.01)
    (Continued)

(52) U.S. Cl.
    CPC .............. *A61B 34/74* (2016.02); *A61B 34/35* (2016.02); *A61B 34/37* (2016.02); *A61B 34/70* (2016.02);
    (Continued)

(58) Field of Classification Search
    CPC ................ A61B 17/29; A61B 2017/29; A61B 2017/00367; A61B 34/30; A61B 34/32;
    (Continued)

(56) References Cited

U.S. PATENT DOCUMENTS 5,752,973 A    5/1998   Kieturakis
5,792,135 A    8/1998   Madhani et al.
         (Continued)

FOREIGN PATENT DOCUMENTS

CN     111481295 A    8/2020
EP      2783653 A1   10/2014
         (Continued)

OTHER PUBLICATIONS

European Search Report for EP Application No. 25 16 7194 mailed Jun. 27, 2025 (11 pages).
         (Continued)

*Primary Examiner* — Tan-Uyen T Ho
*Assistant Examiner* — Lindsey R. Rivers

(57) ABSTRACT

A robotic surgical instrument includes a housing having a shaft extending therefrom. A spring compression assembly is supported within the housing and includes: a proximal hub configured to secure a drive rod disposed therethrough, the proximal hub including teeth; a distal hub spaced from the proximal hub and including teeth; and a compression spring mounted between the proximal and distal hubs. A drive gear includes a proximal portion extending therefrom having threads disposed thereabout configured to engage the teeth of the proximal and distal hubs such that rotation thereof translates the hubs relative to one another and actuates the end effector assembly. A thumb wheel is included that has a portion exposed outside the housing for external manipulation thereof. The thumb wheel is selectively positionable between a disengaged position spaced relative to the drive gear and an engaged position to matingly engage the drive gear.

10 Claims, 36 Drawing Sheets

(51) Int. Cl.

| | |
|---|---|
| *A61B 34/30* | (2016.01) |
| *A61B 34/35* | (2016.01) |
| *A61B 34/37* | (2016.01) |
| *B25J 9/10* | (2006.01) |
| *A61B 18/14* | (2006.01) |
| *A61B 90/00* | (2016.01) |
| *F16J 15/16* | (2006.01) |

(52) U.S. Cl.
CPC ..... *B25J 9/102* (2013.01); *A61B 2017/00367* (2013.01); *A61B 2034/302* (2016.02)

(58) Field of Classification Search
CPC ......... A61B 34/35; A61B 34/37; A61B 34/70; A61B 34/71; A61B 34/72; A61B 34/76; A61B 34/77; A61B 2034/301; A61B 2024/302; A61B 2034/303; A61B 2034/304; A61B 2034/305; A61B 2034/306; A61B 2034/715
See application file for complete search history.

(56) References Cited

U.S. PATENT DOCUMENTS

| | | | |
|---|---|---|---|
| 5,848,986 | A | 12/1998 | Lundquist et al. |
| 6,817,974 | B2 | 11/2004 | Cooper et al. |
| 7,799,028 | B2 | 9/2010 | Schechter et al. |
| 7,861,906 | B2 | 1/2011 | Doll et al. |
| 7,918,230 | B2 | 4/2011 | Whitman et al. |
| 8,579,176 | B2 | 11/2013 | Smith et al. |
| 9,055,961 | B2 | 6/2015 | Manzo et al. |
| 9,474,569 | B2 | 10/2016 | Manzo et al. |
| 10,952,800 | B2 | 3/2021 | Anglese |
| 2002/0099371 | A1 | 7/2002 | Schulze et al. |
| 2002/0177842 | A1 | 11/2002 | Weiss |
| 2003/0125734 | A1 | 7/2003 | Mollenauer |
| 2003/0208186 | A1 | 11/2003 | Moreyra |
| 2006/0022015 | A1 | 2/2006 | Shelton et al. |
| 2006/0025811 | A1 | 2/2006 | Shelton |
| 2006/0161138 | A1 | 7/2006 | Orban et al. |
| 2007/0233052 | A1 | 10/2007 | Brock |
| 2007/0282358 | A1 | 12/2007 | Remiszewski et al. |
| 2008/0015631 | A1 | 1/2008 | Lee et al. |
| 2010/0274265 | A1 | 10/2010 | Wingardner et al. |
| 2010/0292691 | A1 | 11/2010 | Brogna |
| 2011/0118707 | A1 | 5/2011 | Burbank |
| 2011/0118708 | A1 | 5/2011 | Burbank et al. |
| 2011/0118709 | A1 | 5/2011 | Burbank |
| 2011/0118754 | A1 | 5/2011 | Dachs, II et al. |
| 2014/0005676 | A1 | 1/2014 | Shelton et al. |
| 2014/0276723 | A1 | 9/2014 | Parihar et al. |
| 2014/0276761 | A1 | 9/2014 | Parihar |
| 2016/0066982 | A1 | 3/2016 | Marczyk et al. |
| 2017/0042560 | A1 | 2/2017 | Lee et al. |
| 2018/0049737 | A1* | 2/2018 | Swayze ............ A61B 17/07207 |
| 2019/0038279 | A1 | 2/2019 | Shelton, IV et al. |
| 2019/0059989 | A1* | 2/2019 | Heiliger ............. A61B 17/2909 |
| 2019/0183592 | A1* | 6/2019 | Shelton, IV ........... A61B 34/37 |
| 2020/0237453 | A1 | 7/2020 | Anglese |
| 2022/0096066 | A1* | 3/2022 | Beckman ............... A61B 17/00 |

FOREIGN PATENT DOCUMENTS

| | | |
|---|---|---|
| EP | 3689282 A1 | 8/2020 |
| JP | 2016-508747 A | 3/2016 |
| WO | 2016/136628 A1 | 9/2016 |
| WO | 2017053698 A1 | 3/2017 |
| WO | 2017136710 A2 | 8/2017 |

OTHER PUBLICATIONS

CN Office Action for CN Application No. 202110898866.9 mailed Jun. 27, 2025 (9 pages).
JP Notice of Allowance for JP Application No. 2021-129537 mailed Jul. 18, 2025 (2 pages).
Japanese Office Action for JP Application No. 2021-129537 mailed Feb. 7, 2025 (8 pages).

\* cited by examiner

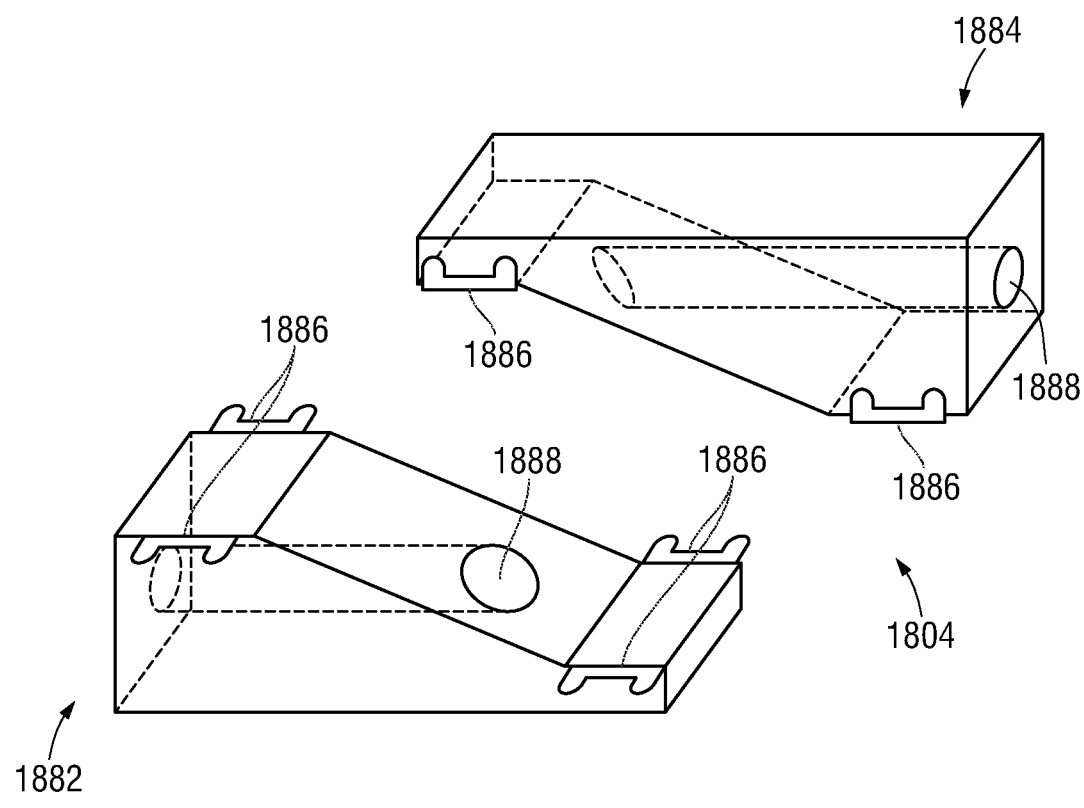
FIG. 18
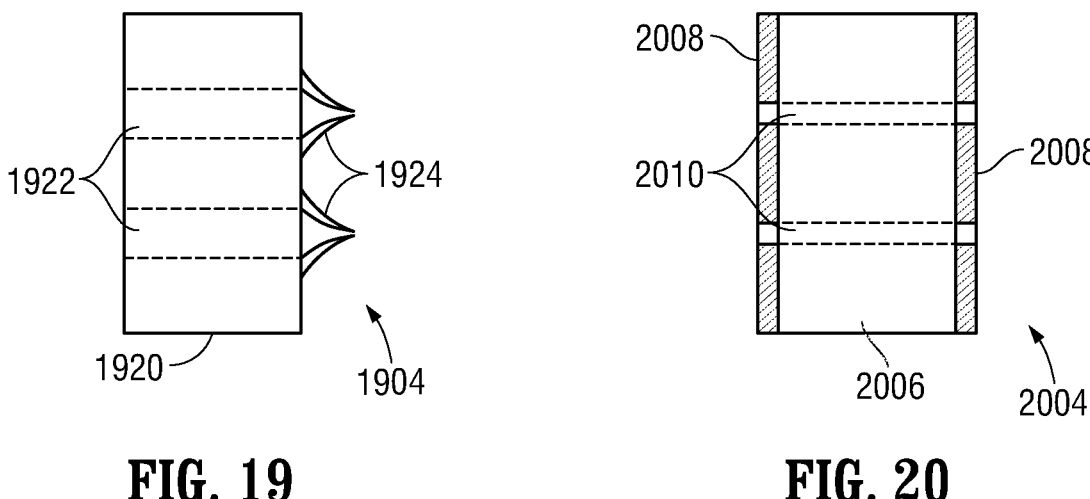
FIG. 19          FIG. 20

2104

62

2105

38

30

2206 2104

62

2204

30

2309 2304

2308

2307

2306

2308

2308

2309

2406

2400

2420

2406

2404

2504

2500

39

39

30

MANUAL END EFFECTOR ACTIVATION FOR ROBOTIC SURGICAL SYSTEMS

CROSS-REFERENCE TO RELATED APPLICATION

This application is a continuation of U.S. patent application Ser. No. 16/988,122, filed on Aug. 7, 2020, the entire contents of which are hereby incorporated herein by reference.

FIELD

The present disclosure relates to surgical instruments and, more specifically, to surgical instruments such as, for example, for use in robotic surgical systems.

BACKGROUND

Robotic surgical systems are increasingly utilized in various different surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

The surgical instruments or portions thereof may be configured as single-use instruments or portions that are discarded after use, or may be configured as reusable instruments or portions that are cleaned and sterilized between uses. Regardless of the configurations of the surgical instruments, the console and robotic arm are capital equipment configured for long-term, repeated use. The console and robotic arm may be protected by a sterile barrier during use and/or wiped clean after use to ensure cleanliness for subsequent uses.

End effector assemblies used for various surgical procedures often need to be manually activatable by the operating staff for cleaning and sterilization and/or for operably engaging various hardware to the robotic instrument. As a result, robotic surgical instruments need to be designed and manufactured with this in mind.

SUMMARY

As used herein, the term "distal" refers to the portion that is being described which is further from an operator (whether a human surgeon or a surgical robot), while the term "proximal" refers to the portion that is being described which is closer to the operator. The terms "about," "substantially," and the like, as utilized herein, are meant to account for manufacturing, material, environmental, use, and/or measurement tolerances and variations, and in any event may encompass differences of up to 10%.

Provided in accordance with aspects of the present disclosure is a robotic surgical instrument including a housing having a shaft extending therefrom having an end effector assembly at a distal end thereof, the shaft including a drive rod extending therethrough configured to actuate the end effector assembly upon translation thereof. A spring compression assembly is supported within the housing, the spring compression assembly including: a proximal hub configured to secure a proximal end of the drive rod disposed therethrough, the proximal hub including a plurality of teeth disposed along an inner peripheral surface thereof; a distal hub spaced from the proximal hub and including a plurality of teeth disposed along an inner peripheral surface thereof; and a compression spring mounted between the proximal and distal hubs. A drive gear is included having a proximal portion extending therefrom including a plurality of threads disposed thereabout configured to matingly engage the corresponding plurality of teeth of the proximal and distal hubs such that rotation thereof translates the proximal and distal hubs relative to one another and actuates the end effector assembly. A thumb wheel is included having a portion thereof exposed outside the housing for external manipulation thereof. The thumb wheel is selectively positionable between a first, disengaged position spaced relative to the drive gear and a second, engaged position to matingly engage the drive gear and allow manual actuation of the end effector assembly.

In aspects according to the present disclosure, the drive gear is configured to matingly engage a corresponding gear of an input shaft that operably connects to a drive input adapted to connect to a robot surgical system.

In aspects according to the present disclosure, the thumb wheel is biased in the disengaged position. In other aspects according to the present disclosure, moving the thumb wheel relative to the housing and rotating the thumb wheel correspondingly rotates the drive gear which, in turn, translates the proximal hub relative to the distal hub to actuate the end effector assembly. In yet other aspects according to the present disclosure, translation of the proximal hub relative to the distal hub moves the drive rod to actuate the end effector assembly.

In aspects according to the present disclosure, moving the thumb wheel relative to the housing and rotating the thumb wheel correspondingly rotates the drive gear which, in turn, rotates a corresponding gear of an input shaft that operably connects to a drive input adapted to connect to a robot surgical system.

In aspects according to the present disclosure, the end effector assembly includes a pair of first and second jaw members, at least one of the jaw members moveable relative to the other jaw member.

Provided in accordance with aspects of the present disclosure is a robotic surgical instrument including a housing having a shaft extending therefrom including an end effector assembly at a distal end thereof, the shaft including a drive rod extending therethrough configured to actuate the end effector assembly upon translation thereof. A spring compression assembly is supported within the housing, the spring compression assembly including: a proximal hub configured to secure a proximal end of the drive rod disposed therethrough, the proximal hub including a plurality of teeth disposed along an inner peripheral surface thereof; a distal hub spaced from the proximal hub and including a plurality of teeth disposed along an inner peripheral surface thereof; and a compression spring mounted between the proximal and distal hubs. A drive gear is included having a proximal portion extending therefrom including a plurality of threads disposed thereabout configured to matingly engage the corresponding plurality of teeth of the proximal and distal hubs such that rotation thereof translates the proximal and distal hubs relative to one another and actuates the end effector assembly. A drive input is included having a drive input shaft having an input gear configured to matingly engage the drive gear such that rotation of the drive input shaft correspondingly rotates the drive gear, the drive input shaft including a mechanical interface disposed thereabout. A thumb wheel is included having a portion thereof exposed outside the housing for external manipulation thereof. The thumb wheel includes a corresponding mechanical interface disposed about an inner periphery thereof, the mechanical interface of the drive input shaft configured to matingly engage the corresponding mechanical interface of the thumb wheel upon selective translation of the thumb wheel. The thumb wheel is selectively translatable between a first, disengaged position spaced relative to the mechanical interface disposed on the drive input shaft and a second, engaged position to matingly engage the thumb wheel with the drive input shaft and allow manual actuation of the end effector assembly.

In aspects according to the present disclosure, the thumb wheel is biased in the disengaged position. In other aspects according to the present disclosure, translating the thumb wheel along the drive input shaft and rotating the thumb wheel correspondingly rotates the drive input shaft and the drive gear which, in turn, translates the proximal hub relative to the distal hub to actuate the end effector assembly. In yet other aspects according to the present disclosure, translation of the proximal hub relative to the distal hub moves the drive rod to actuate the end effector assembly.

In aspects according to the present disclosure, the end effector assembly includes a pair of first and second jaw members, at least one of the jaw members moveable relative to the other jaw member. In aspects according to the present disclosure, the drive input shaft includes a plurality of castellations defined thereabout that is configured to matingly engage a corresponding plurality of teeth disposed along an inner peripheral surface of the thumb wheel upon selective translation of the thumb wheel.

In aspects according to the present disclosure, the thumb wheel is disposed distally of the spring compression assembly. In other aspects according to the present disclosure, movement of the thumb wheel distally engages the plurality of teeth with the corresponding plurality of castellations defined about the drive input shaft.

BRIEF DESCRIPTION OF THE DRAWINGS

Various aspects and features of the present disclosure are described hereinbelow with reference to the drawings wherein:

FIG. 18 is an exploded perspective view of another seal in accordance with the present disclosure;

FIGS. 19 and 20 are side views of still other seals in accordance with the present disclosure;

DETAILED DESCRIPTION

Figure 1:
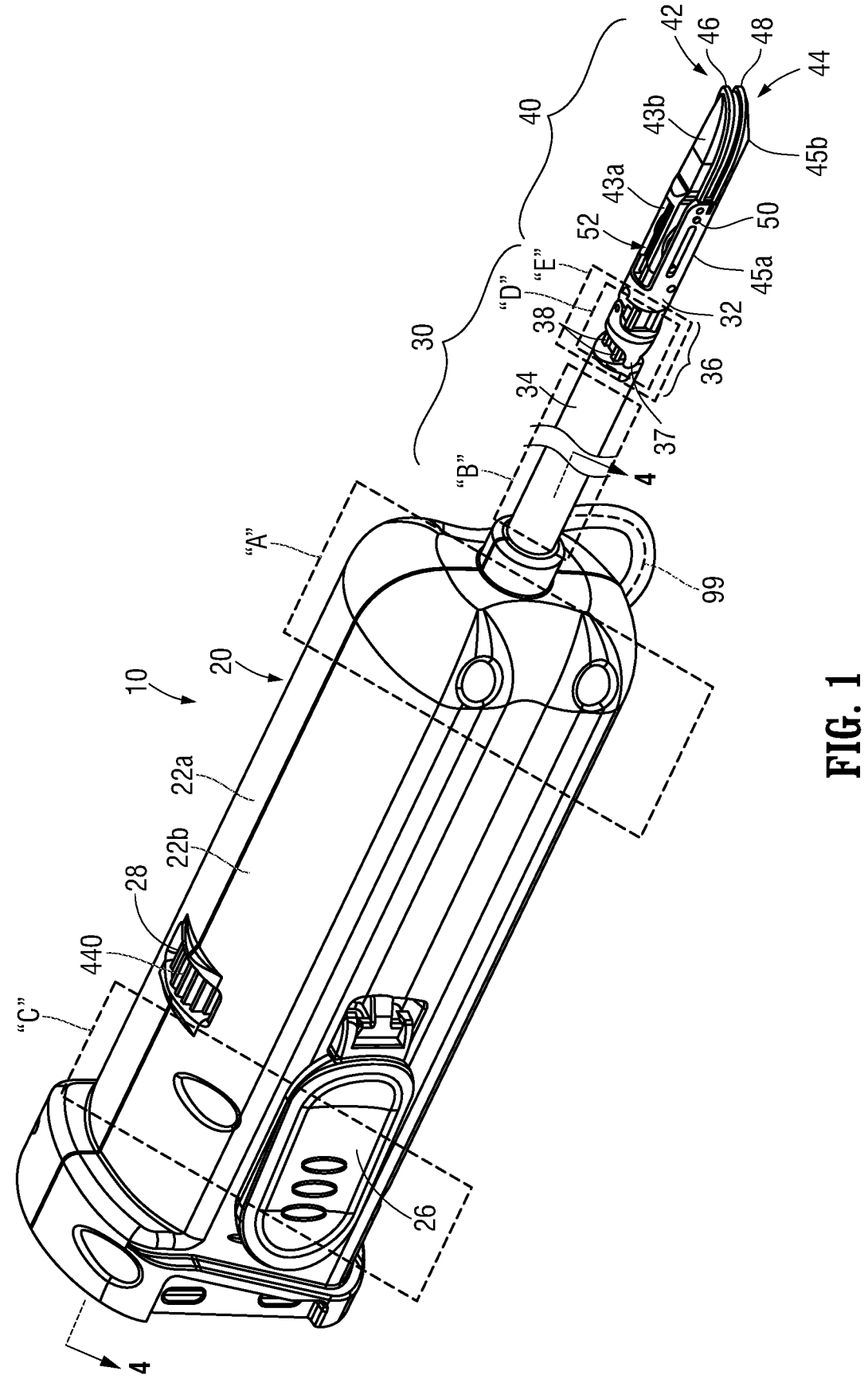
FIG. 1 is a perspective view of a surgical instrument provided in accordance with the present disclosure configured for mounting on a robotic arm of a robotic surgical system.
Figure 2A:
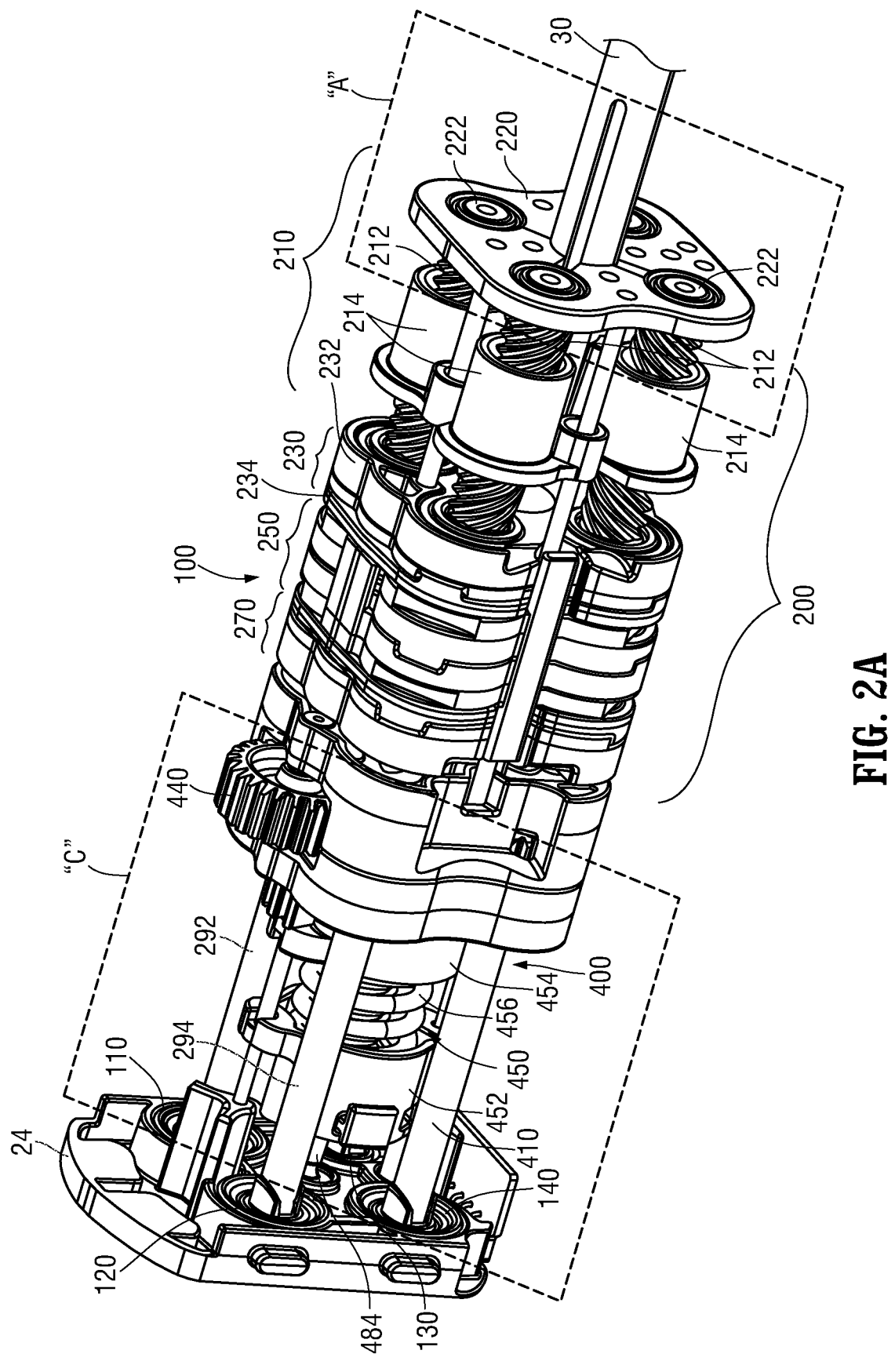
FIG. 2A is a front perspective view of a proximal portion of the surgical instrument of FIG. 1 with an outer housing removed.
Figure 2B:
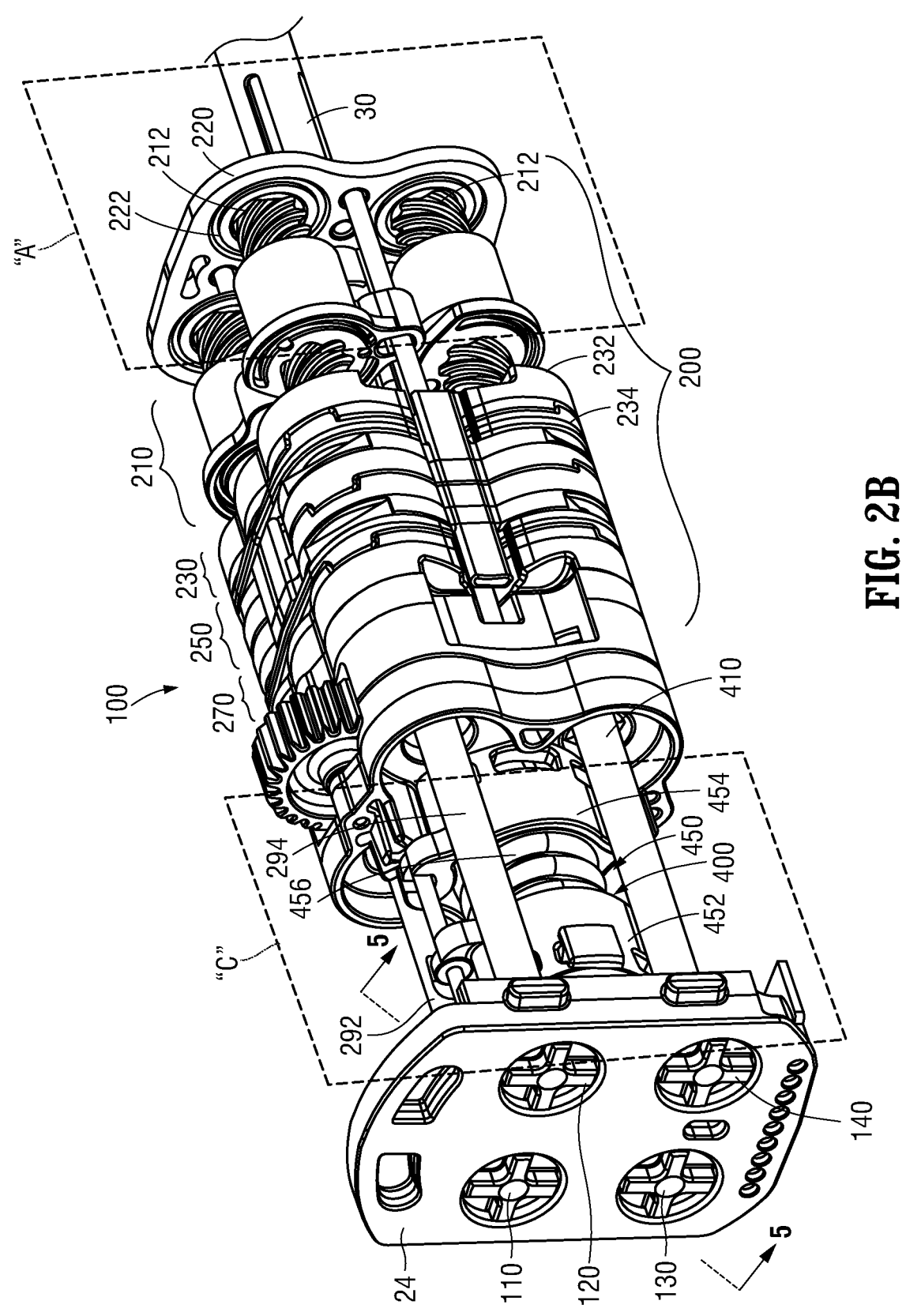
FIG. 2B is a rear perspective view of the proximal portion of the surgical instrument of FIG. 1 with the outer housing removed.
Figure 2C:
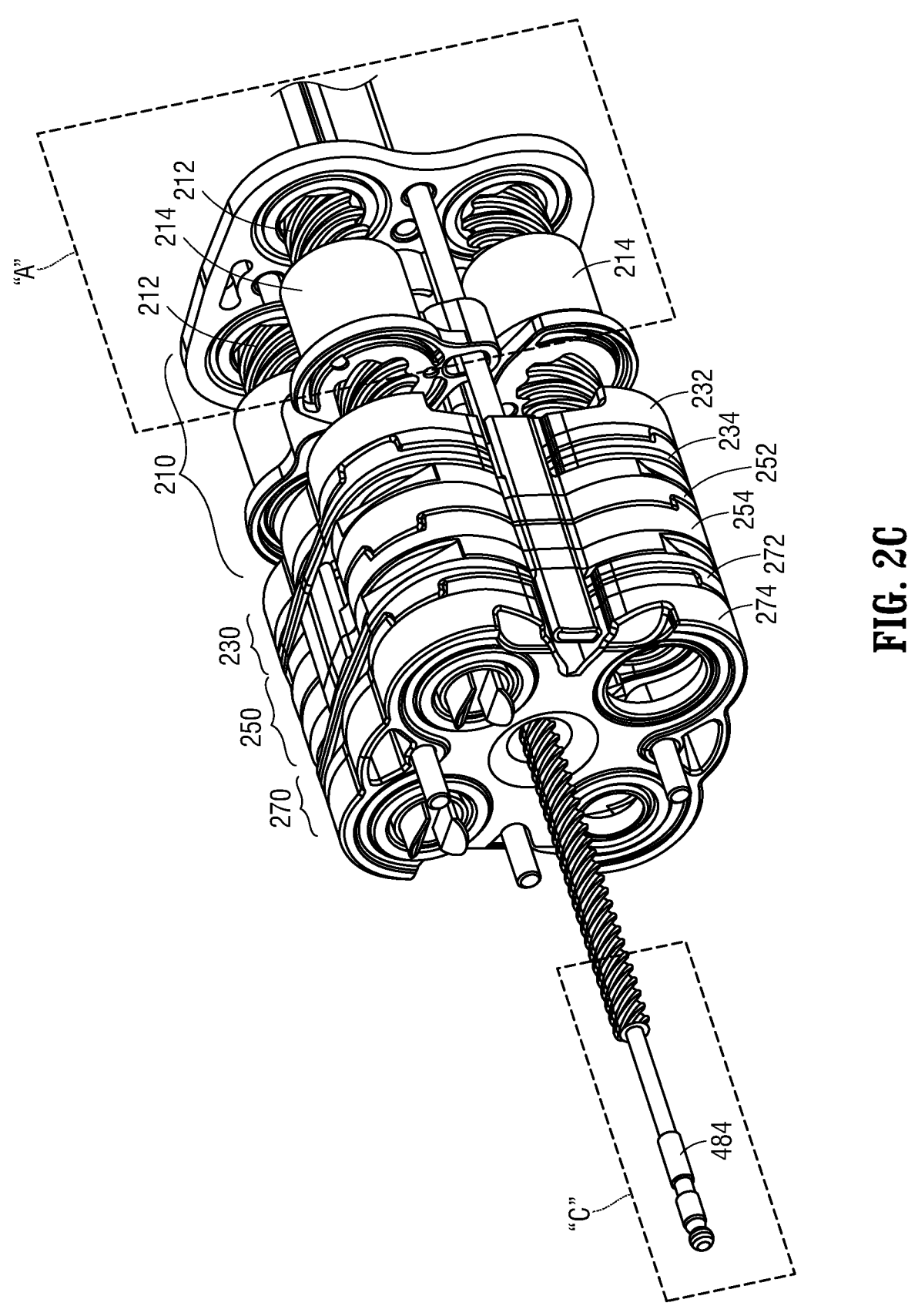
FIG. 2C is a rear perspective view of the proximal portion of the surgical instrument of FIG. 1 with the outer housing and proximal components of the actuation assembly removed.
Figure 3:
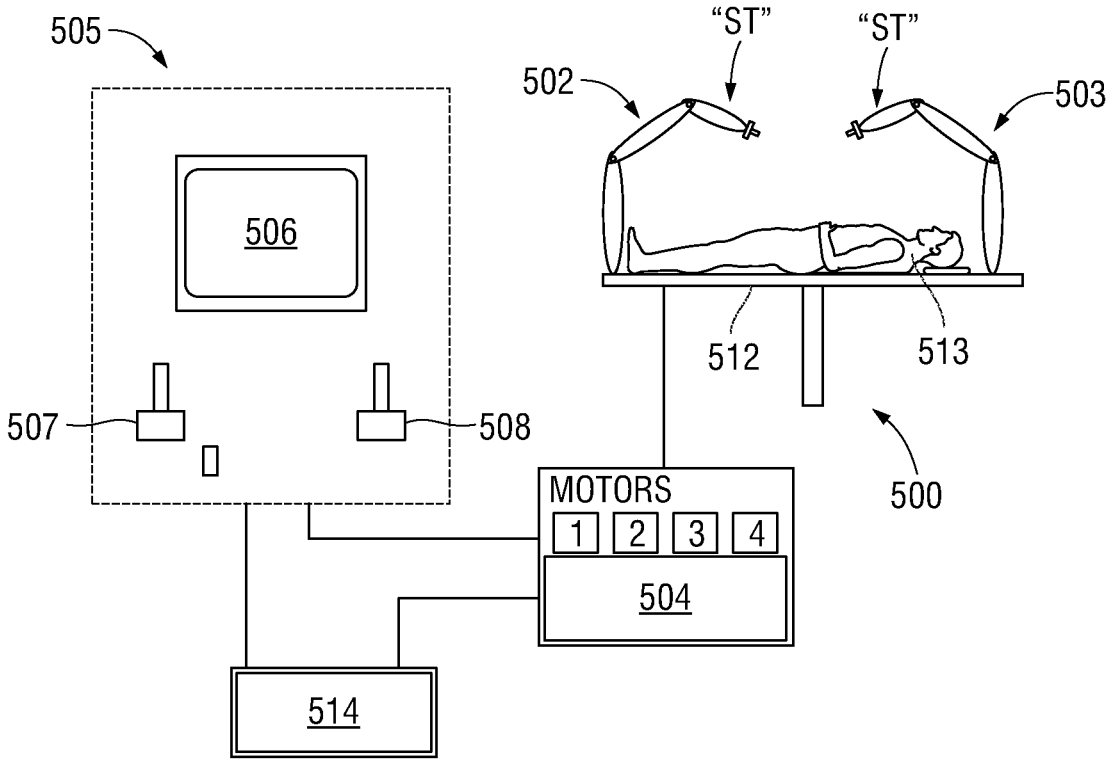
FIG. 3 is a schematic illustration of an exemplary robotic surgical system configured to releasably receive the surgical instrument of FIG. 1.

Referring to FIGS. 1-2C, a surgical instrument 10 provided in accordance with the present disclosure generally includes a housing 20, a shaft 30 extending distally from housing 20, an end effector assembly 40 extending distally from shaft 30, and an actuation assembly 100 disposed within housing 20 and operably associated with shaft 30 and end effector assembly 40. Instrument 10 is detailed herein as an articulating electrosurgical forceps configured for use with a robotic surgical system, e.g., robotic surgical system 500 (FIG. 3). However, the aspects and features of instrument 10 provided in accordance with the present disclosure, detailed below, are equally applicable for use with other suitable surgical instruments and/or in other suitable surgical systems.

Housing 20 of instrument 10 includes first and second body portion 22a, 22b and a proximal face plate 24 that cooperate to enclose actuation assembly 100 therein. Proximal face plate 24 includes apertures defined therein through which inputs 110-140 of actuation assembly 100 extend. A pair of latch levers 26 (only one of which is illustrated in FIG. 1) extends outwardly from opposing sides of housing 20 and enables releasable engagement of housing 20 with a robotic arm of a surgical system, e.g., robotic surgical system 500 (FIG. 3). An aperture 28 defined through housing 20 permits thumbwheel 440 to extend therethrough to enable manual manipulation of thumbwheel 440 from the exterior of housing 20 to permit manual opening and closing of end effector assembly 40.

Shaft 30 of instrument 10 includes a distal segment 32, a proximal segment 34, and an articulating section 36 disposed between the distal and proximal segments 32, 34, respectively. Articulating section 36 includes one or more articulating components 37, e.g., links, joints, etc. A plurality of articulation cables 38, e.g., four (4) articulation cables, or other suitable actuators, extends through articulating section 36. More specifically, articulation cables 38 are operably coupled to distal segment 32 of shaft 30 at the distal ends thereof and extend proximally from distal segment 32 of shaft 30, through articulating section 36 of shaft 30 and proximal segment 34 of shaft 30, and into housing 20, wherein articulation cables 38 operably couple with an articulation assembly 200 of actuation assembly 100 to enable selective articulation of distal segment 32 (and, thus end effector assembly 40) relative to proximal segment 34 and housing 20, e.g., about at least two axes of articulation (yaw and pitch articulation, for example). Articulation cables 38 are arranged in a generally rectangular configuration, although other suitable configurations are also contemplated.

With respect to articulation of end effector assembly 40 relative to proximal segment 34 of shaft 30, actuation of articulation cables 38 is effected in pairs. More specifically, in order to pitch end effector assembly 40, the upper pair of cables 38 is actuated in a similar manner while the lower pair of cables 38 is actuated in a similar manner relative to one another but an opposite manner relative to the upper pair of cables 38. With respect to yaw articulation, the right pair of cables 38 is actuated in a similar manner while the left pair of cables 38 is actuated in a similar manner relative to one another but an opposite manner relative to the right pair of cables 38.

End effector assembly 40 includes first and second jaw members 42, 44, respectively. Each jaw member 42, 44 includes a proximal flange portion 43a, 45a and a distal body portion 43b, 45b, respectively. Distal body portions 43b, 45b define opposed tissue-contacting surfaces 46, 48, respectively. Proximal flange portions 43a, 45a are pivotably coupled to one another about a pivot 50 and are operably coupled to one another via a cam-slot assembly 52 including a cam pin slidably received within cam slots defined within the proximal flange portion 43a, 45a of at least one of the jaw members 42, 44, respectively, to enable pivoting of jaw member 42 relative to jaw member 44 and distal segment 32 of shaft 30 between a spaced-apart position (e.g., an open position of end effector assembly 40) and an approximated position (e.g. a closed position of end effector assembly 40) for grasping tissue between tissue-contacting surfaces 46, 48. As an alternative to this unilateral configuration, a bilateral configuration may be provided whereby both jaw members 42, 44 are pivotable relative to one another and distal segment 32 of shaft 30.

Figure 4:
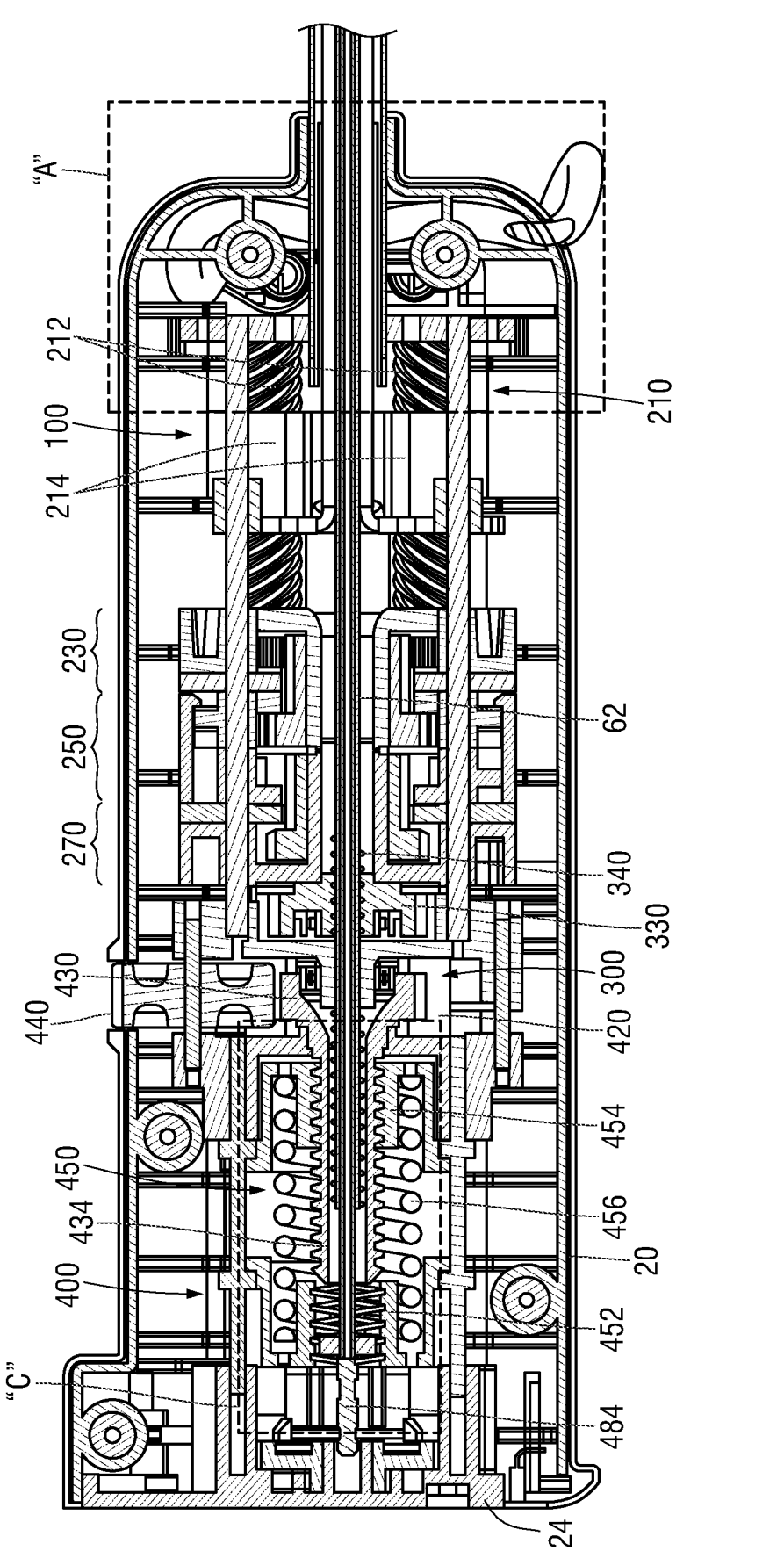
FIG. 4 is a longitudinal cross-sectional view taken along section line "4-4" of FIG. 1.

In some configurations, longitudinally-extending knife channels (not shown) are defined through tissue-contacting surfaces 46, 48, respectively, of jaw members 42, 44. In such configurations, a knife assembly 60 is provided that includes a proximal knife drive tube 62, a distal knife rod 64, an intermediate elongated collar 66, and a knife blade 68 (see FIGS. 26A, 26B and 29A). The connector components 62-66 of knife assembly 60 (see FIGS. 26A, 26B and 29A) extend from housing 20 through shaft 30 to end effector assembly 40. Knife blade 68 (FIG. 29A) is disposed within end effector assembly 40 between jaw members 42, 44 is provided to enable cutting of tissue grasped between tissue-contacting surfaces 46, 48 of jaw members 42, 44, respectively. Proximal knife tube 62 (FIGS. 4 and 26A-26B) is operably coupled to a knife drive assembly 300 of actuation assembly 100 (FIGS. 2A and 2B) at a proximal end thereof to enable selective actuation thereof to, in turn, reciprocate the knife blade 68 (FIG. 29A) between jaw members 42, 44 to cut tissue grasped between tissue-contacting surfaces 46, 48.

Continuing with reference to FIGS. 1-2C, a drive rod 484 is operably coupled to cam-slot assembly 52 of end effector assembly 40, e.g., engaged with the cam pin thereof, such that longitudinal actuation of drive rod 484 pivots jaw member 42 relative to jaw member 44 between the spaced-apart and approximated positions. More specifically, urging drive rod 484 proximally pivots jaw member 42 relative to jaw member 44 towards the approximated position while urging drive rod 484 distally pivots jaw member 42 relative to jaw member 44 towards the spaced-apart position. However, other suitable mechanisms and/or configurations for pivoting jaw member 42 relative to jaw member 44 between the spaced-apart and approximated positions in response to selective actuation of drive rod 484 are also contemplated. Drive rod 484 extends proximally from end effector assembly 40 through shaft 30 and into housing 20 wherein drive rod 484 is operably coupled with a jaw drive assembly 400 of actuation assembly 100 (FIGS. 2A and 2B) to enable selective actuation of end effector assembly 40 to grasp tissue therebetween and apply a closure force within an appropriate jaw closure force range.

Tissue-contacting surfaces 46, 48 of jaw members 42, 44, respectively, are at least partially formed from an electrically conductive material and are energizable to different potentials to enable the conduction of electrical energy through tissue grasped therebetween, although tissue-contacting surfaces 46, 48 may alternatively be configured to supply any suitable energy, e.g., thermal, microwave, light, ultrasonic, etc., through tissue grasped therebetween for energy-based tissue treatment. Instrument 10 defines a conductive pathway (not shown) through housing 20 and shaft 30 to end effector assembly 40 that may include lead wires 99, contacts, and/or electrically-conductive components to enable electrical connection of tissue-contacting surfaces 46, 48 of jaw members 42, 44, respectively, to an energy source (not shown), e.g., an electrosurgical generator via an electrosurgical cable extending therebetween, for supplying energy to tissue-contacting surfaces 46, 48 to treat, e.g., seal, tissue grasped between tissue-contacting surfaces 46, 48.

Figure 5:
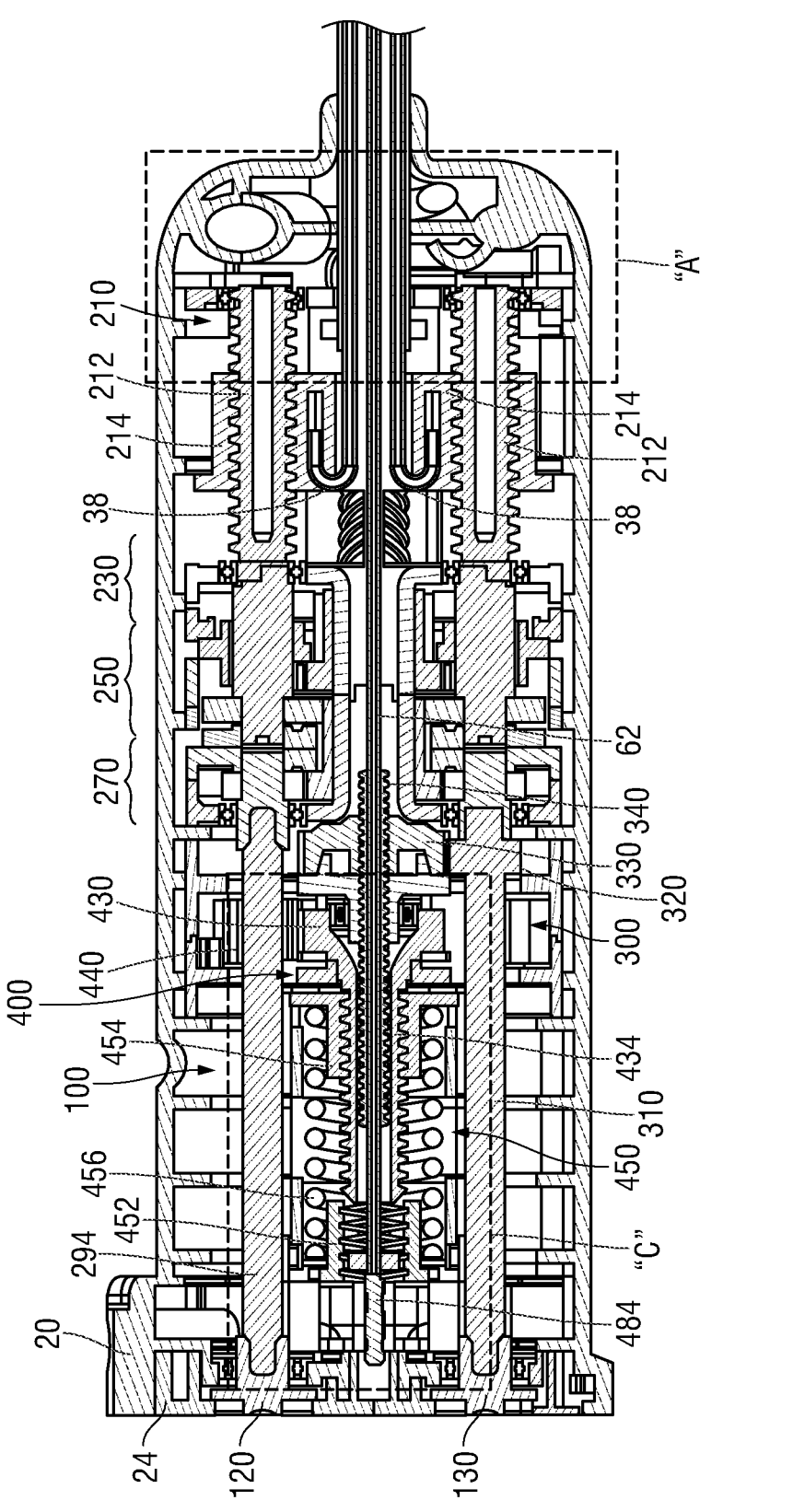
FIG. 5 is a longitudinal cross-sectional view taken along section line "5-5" of FIG. 2B.

As noted above, actuation assembly 100 is disposed within housing 20 and includes an articulation assembly 200, a knife drive assembly 300, and a jaw drive assembly 400. Articulation assembly 200 is operably coupled between first and second inputs 110, 120, respectively, of actuation assembly 100 and articulation cables 38 (FIG. 1) such that, upon receipt of appropriate rotational inputs into first and/or second inputs 110, 120, articulation assembly 200 manipulates cables 38 (FIGS. 1 and 5) to articulate end effector assembly 40 in a desired direction, e.g., to pitch and/or yaw end effector assembly 40. Knife drive assembly 300 is operably coupled between third input 130 of actuation assembly 100 and knife tube 62 (FIGS. 26A and 26B) such that, upon receipt of appropriate rotational input into third input 130, knife drive assembly 300 manipulates knife tube 62 to reciprocate the knife blade 68 (FIG. 29A) between jaw members 42, 44 to cut tissue grasped between tissue-contacting surfaces 46, 48. Jaw drive assembly 400 is operably coupled between fourth input 140 of actuation assembly 100 and drive rod 484 such that, upon receipt of appropriate rotational input into fourth input 140, jaw drive assembly 400 pivots jaw members 42, 44 between the spaced-apart and approximated positions to grasp tissue therebetween and apply a closure force within an appropriate closure force range.

Actuation assembly 100 is configured to operably interface with a robotic surgical system 500 (FIG. 3) when instrument 10 is mounted on robotic surgical system 500 (FIG. 3), to enable robotic operation of actuation assembly 100 to provide the above-detailed functionality. That is, robotic surgical system 500 (FIG. 3) selectively provides rotational inputs to inputs 110-140 of actuation assembly 100 to articulate end effector assembly 40, grasp tissue between jaw members 42, 44, and/or cut tissue grasped between jaw members 42, 44. However, it is also contemplated that actuation assembly 100 be configured to interface with any other suitable surgical system, e.g., a manual surgical handle, a powered surgical handle, etc. For the purposes herein, robotic surgical system 500 (FIG. 3) is generally described.

Turning to FIG. 3, robotic surgical system 500 is configured for use in accordance with the present disclosure. Aspects and features of robotic surgical system 500 not germane to the understanding of the present disclosure are omitted to avoid obscuring the aspects and features of the present disclosure in unnecessary detail.

Robotic surgical system 500 generally includes a plurality of robot arms 502, 503; a control device 504; and an operating console 505 coupled with control device 504. Operating console 505 may include a display device 506, which may be set up in particular to display three-dimensional images; and manual input devices 507, 508, by means of which a person, e.g., a surgeon, may be able to telemanipulate robot arms 502, 503 in a first operating mode. Robotic surgical system 500 may be configured for use on a patient 513 lying on a patient table 512 to be treated in a minimally invasive manner. Robotic surgical system 500 may further include a database 514, in particular coupled to control device 504, in which are stored, for example, preoperative data from patient 513 and/or anatomical atlases.

Each of the robot arms 502, 503 may include a plurality of members, which are connected through joints, and a mounted device which may be, for example, a surgical tool "ST." One or more of the surgical tools "ST" may be instrument 5 (FIG. 1), thus providing such functionality on a robotic surgical system 500.

Robot arms 502, 503 may be driven by electric drives, e.g., motors, connected to control device 504. Control device 504, e.g., a computer, may be configured to activate the motors, in particular by means of a computer program, in such a way that robot arms 502, 503, and, thus, their mounted surgical tools "ST" execute a desired movement and/or function according to a corresponding input from manual input devices 507, 508, respectively. Control device 504 may also be configured in such a way that it regulates the movement of robot arms 502, 503 and/or of the motors.

With reference to FIGS. 1, 2A-2C, 4, and 5, articulation assembly 200 of actuation assembly 100 including a lead screw sub-assembly 210, a first gear sub-assembly 230, a second gear sub-assembly 250, a third gear sub-assembly 270, and first and second input shafts 292, 294. Although articulation assembly 200 is detailed herein as including a plurality of gears, such gearing components may be replaced or supplemented with the use of belts instead of directly meshed gears, without departing from the present disclosure.

Further, multiple gears (and/or belts) may be provided in place of single gears (and/or belts) to provide a desired amplification or attenuation effect.

Lead screw sub-assembly 210 of actuation assembly 100 includes four lead screws 212 arranged to define a generally square configuration wherein diagonally-opposed lead screws 212 define opposite thread-pitch directions. Each lead screw 212 includes a collar 214 threadingly engaged thereabout such that rotation of the lead screw 212 translates the corresponding collar 214 longitudinally therealong. Each collar 214, in turn, secures a proximal end portion of one of the articulation cables 38 therein, e.g., via a crimp or other suitable engagement (mechanical fastening, adhesion, welding, etc.). Thus, distal translation of a collar 214 slackens the corresponding articulation cable 38 by pushing the corresponding articulation cable 38 in a distal direction, while proximal translation of a collar 214 tensions the corresponding articulation cable 38 by pulling the corresponding articulation cable 38 in a proximal direction.

Lead screw sub-assembly 210 further includes a distal plate 220 including four bushings 222 each of which rotatably retains the distal end portion of one of the four lead screws 212. The proximal end portions of lead screws 212 define keyed, e.g., semi-circular, inputs, such that rotational inputs provided thereto similarly rotate the lead screws 212. In some configurations, a proximal end portion of shaft 30 is fixedly engaged (directly or indirectly) with distal plate 220.

First gear sub-assembly 230 includes a distal housing body 232 and a proximal housing body 234 that cooperate to operably support a first pair of diagonally-opposed gears mounted on keyed outputs such that such that rotation of one of the gears rotates the corresponding keyed output. The proximal end portions of a first diagonally-opposed pair of lead screws 212 of lead screw sub-assembly 210 are engaged with corresponding keyed outputs of first gear sub-assembly 230, thereby rotatably coupling each of the gears of first gear sub-assembly 230 with one of the lead screws 212 of the first diagonally-opposed pair of lead screws 212 such that rotation of one of the gears rotates the corresponding lead screw 212.

Second gear sub-assembly 250 includes a distal housing body 252 and a proximal housing body 254 that cooperate to operably support a second pair of diagonally-opposed gears mounted on keyed outputs, a central compound gear, and a first coupling gear mounted on a first coupling shaft. The first coupling gear 264 is disposed in meshed engagement with a proximal gear of the central compound gear.

The first diagonal pair of articulation cables 38 is pre-tensioned prior to engagement of second gear sub-assembly 250 with first gear sub-assembly 230. Upon such engagement, the keyed outputs of second gear sub-assembly 250 are rotationally coupled with the proximal end portions of the second diagonally-opposed pair of lead screws 212, thereby rotatably coupling each of the gears of second gear sub-assembly 250 with one of the lead screws 212 of the second diagonally-opposed pair of lead screws 212 such that rotation of one of the gears rotates the corresponding lead screw 212. Engagement of second gear sub-assembly 250 with first gear sub-assembly 230 also disposes a distal gear of the central compound gear into meshed engagement with and between the diagonally-opposed gears of first gear sub-assembly 230 to thereby couple the diagonally-opposed gears with one another, coupling the lead screws 212 of the first diagonally-opposed pair of lead screws 212 with one another and locking in the pre-tension of the first pair of articulation cables 38.

Third gear sub-assembly 270 includes a distal housing body 272 and a proximal housing body 274 that operably support a central compound gear and a second coupling gear mounted on a second coupling shaft. The second coupling shaft includes the second coupling gear mounted thereon and has a proximal end portion that defines a keyed input. Prior to engagement of third gear sub-assembly 270 with second gear sub-assembly 250, the second diagonal pair of articulation cables 38 is pre-tensioned. Once the pre-tension threshold for the second diagonal pair of articulation cables 38 is reached, third gear sub-assembly 270 is engaged with second gear sub-assembly 250 such that a distal gear of the central compound gear of third gear sub-assembly 270 is disposed in meshed engagement with and between the second pair of diagonally-opposed gears of second gear sub-assembly 250 to couple the diagonally-opposed gears with one another, thereby coupling the second diagonally-opposed pair of lead screws 212 with one another, and locking the pre-tension on the second pair of articulation cables 38.

With first, second, and third gear sub-assemblies 230, 250, 270, respectively, assembled with one another and lead screw sub-assembly 210, as detailed above, input shafts 292, 294 can be connected between inputs 110, 120 and the keyed outputs of first and second gear sub-assemblies 230, 240, respectively. Thus, in use, rotational input provided to inputs 110, 120 can be utilized to move collars 214 about lead screws 212 in diagonal pairs. Depending upon the direction of rotational input provided to inputs 110, 120 and whether the inputs to the pairs are the same or opposite, pitch articulation (in either direction), yaw articulation (in either direction), and/or any combination thereof can be achieved. Articulation assembly 200 is described in greater detail in U.S. patent application Ser. No. 16/395,748, titled "ARTICULATION ASSEMBLY FOR A SURGICAL INSTRUMENT SUCH AS FOR USE IN A ROBOTIC SURGICAL SYSTEM AND METHODS OF ASSEMBLING THE SAME," filed on Apr. 26, 2019.

Continuing with reference to FIGS. 1, 2A-2C, 4, and 5, knife drive assembly 300 includes an input shaft 310, an input gear 320 engaged on input shaft 310, a central gear 330 defining external threading disposed in meshed engagement with input gear 320 and internal threading, and a lead screw 340 extending through the central gear 330 in meshed engagement with the internal threading thereof. As a result of this configuration, a rotational input provided to third input 130 rotates input shaft 310, thereby rotating input gear 320 to, in turn, rotate central gear 330, which results in translation of lead screw 340. Lead screw 340 is fixedly engaged about a proximal end portion of knife tube 62 such that translation of lead screw 340 translates knife tube 62, e.g., to thereby translate the knife blade 68 (FIG. 29A) between jaw members 42, 44 (FIG. 1) to cut tissue grasped therebetween. Lead screw 340 and knife tube 62 are coaxially disposed about drive rod 484.

Jaw drive assembly 400 includes an input shaft 410 operably coupled to fourth input 140 at a proximal end portion thereof, an input gear 420 fixedly engaged on input shaft 410 at a distal end portion thereof, a drive gear 430 disposed in meshed engagement with input gear 420, a thumbwheel 440 disposed in meshed engagement with drive gear 430, a lead screw 434 is fixedly engaged, e.g., monolithically formed with, drive gear 430, and a spring force assembly 450 operably coupling lead screw 434 with drive rod 484. Spring force assembly 450 includes a proximal hub 452 engaged with a proximal end portion of drive rod 484, a distal hub 454 threadingly engaged about lead screw 434, and a compression spring 456 disposed between proximal and distal hubs 452, 454, respectively. As a result of this configuration, in response to an input to close end effector assembly 40, e.g., rotational input to fourth input 140 or a manual input to rotation wheel 440, drive shaft 410 is rotated to thereby rotate input gear 420 which, in turn, rotates drive gear 430 such that distal hub 454 is translated proximally towards proximal hub 452. Initially, where forces resisting approximation of jaw members 42, 44 are below a threshold corresponding to the spring value of compression spring 456, the closure force applied by jaw members 42, 44 is relatively 18*w* such that the urging of distal hub 454 proximally against compression spring 456 urges compression spring 456 proximally which, in turn, urges drive rod 484 proximally to pivot jaw member 42 relative to jaw member 44 from the spaced-apart position towards the approximated position to grasp tissue therebetween. Upon further approximation of jaw members 42, 44 to grasp tissue therebetween, the forces resisting approximation of jaw members 42, 44, e.g., tissue resisting compression, may reach the threshold and, thus the closure force applied by jaw members 42, 44 may reach a corresponding threshold. In order to maintain the closure force applied by jaw members 42, 44 within a closure force range such as, for example, from about 3 kg/cm² to about 16 kg/cm², application of further closure force by jaw members 42, 44 is inhibited beyond this point despite further rotational input to fourth input 140. More specifically, once the threshold has been reached, further rotational input to fourth input 140 rotates drive shaft 410, input gear 420, and drive gear 430 to translate distal hub 454 further proximally into compression spring 456. However, rather than compression spring 456 urging proximal hub 452 further proximally to continue approximation of jaw members 42, 44 and increase the closure force applied therebetween, compression spring 456 is compressed, enabling proximal hub 452 and, thus, drive rod 484 to remain in position despite the continued movement of distal hub 454, thus inhibiting application of additional closure force between jaw members 42, 44. With tissue grasped between jaw members 42, 44 under an appropriate closure force, energy may be supplied to jaw members 42, 44 to treat, e.g., seal tissue. Thereafter, the knife 68 (FIG. 29A) may be advanced between jaw members 42, 44 to cut the treated tissue.

Figure 6:
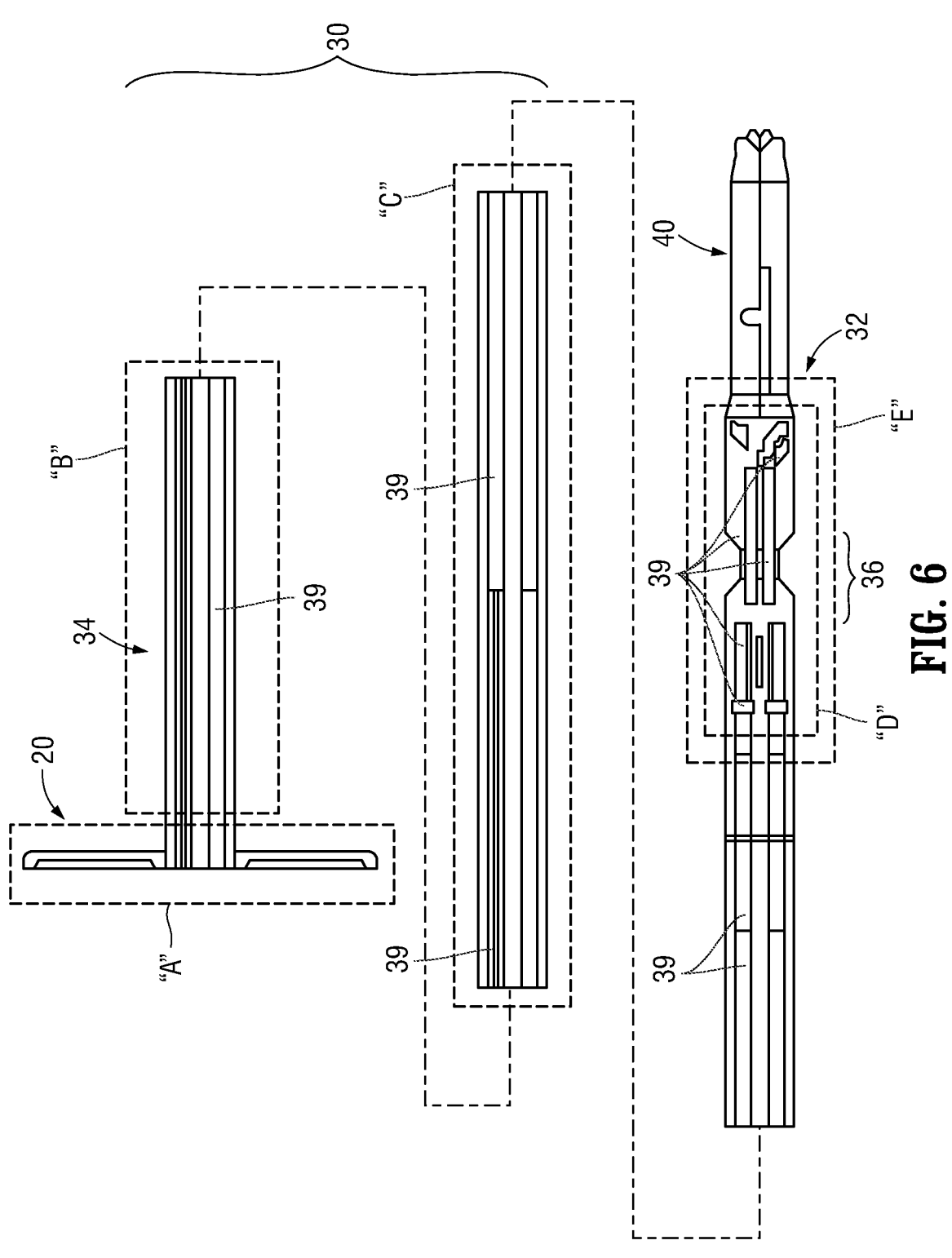
FIG. 6 is longitudinal cross-sectional view of a distal portion of the surgical instrument of FIG. 1.

Turning to FIG. 6, in conjunction with FIG. 1, as noted above, shaft 30 extends distally from housing 20 and includes distal segment 32, proximal segment 34, and articulating section 36. In some configurations, as also noted above, a proximal end portion of proximal segment 34 of shaft 30 extends into housing 20 wherein it is fixedly engaged (directly or indirectly) with distal plate 220 of articulation assembly 200 (see FIG. 2A) within housing 20. Articulation cables 38 (FIGS. 1, 4, and 5), knife tube 62 (FIGS. 4 and 5), and electrically-conductive structures (e.g., lead wires 99 (FIG. 1)) extend through proximal segment 34 of shaft 30 to articulating section 36, distal segment 32, or end effector assembly 40 to enable articulation of end effector assembly 40 in pitch and jaw directions and to enable operation of end effector assembly 40 to grasp, treat, and/or cut tissue. In order to provide support for these components extending through shaft 30 and maintain proper position, spacing, and/or orientation of these components extending through shaft 30, one or more internal structures 39 are disposed or formed within shaft 30. The one or more internal structures 39 may include, for example, any combination of one or more of supports, spacers, guides, bushings, etc., and may extend along a portion or the entirety of shaft 30 continuously or intermittently.

Referring generally to FIGS. 1-6, during use of instrument 10, fluids (blood, other bodily fluids, surgical fluids, etc., including fluids carrying tissue, surgical debris, etc.) from the surgical site may enter instrument 10, e.g., via end effector assembly 40, articulating section 36 of shaft 30, and/or at other locations, and travel proximally within and/or about shaft 30 towards or into housing 20. In order to protect capital equipment such as the robotic arm of the robotic surgical system, e.g., robotic surgical system 500 (FIG. 3), to which instrument 10 is mounted (and/or for other purposes such as, for example, to facilitate cleaning all or a portion of instrument 10 in preparation for reuse), the present disclosure provides various seal configurations (one-part seals, multi-part seals, plural seals, seal assemblies including one or more seals and one or more support/retention parts, etc.) disposed in various different locations along instrument 10 to inhibit proximally-traveling fluid from contaminating the robotic arm (and/or portions of instrument 10).

More specifically, one or more seals may be disposed at one or more of the following locations: location "A" at a proximal end portion of shaft 30 within or adjacent to housing 20; location "B" at one or more positions along a portion of proximal segment 34 of shaft 30; location "C" at or near proximal end portions of knife assembly 60, knife drive assembly 300, and/or jaw drive assembly 400; location "D" at or near distal end portions of knife assembly 60 and/or jaw drive assembly 400; and/or location "E" at or near articulating section 36 of shaft 30. Further, although a seal may be detailed herein for use at one location, it is contemplated that any such seals, to the extent practicable, may be used at any of the other identified locations or other suitable locations. Likewise, any suitable combination of seals at one or more of the identified locations and/or other suitable locations may be provided.

Figure 7:
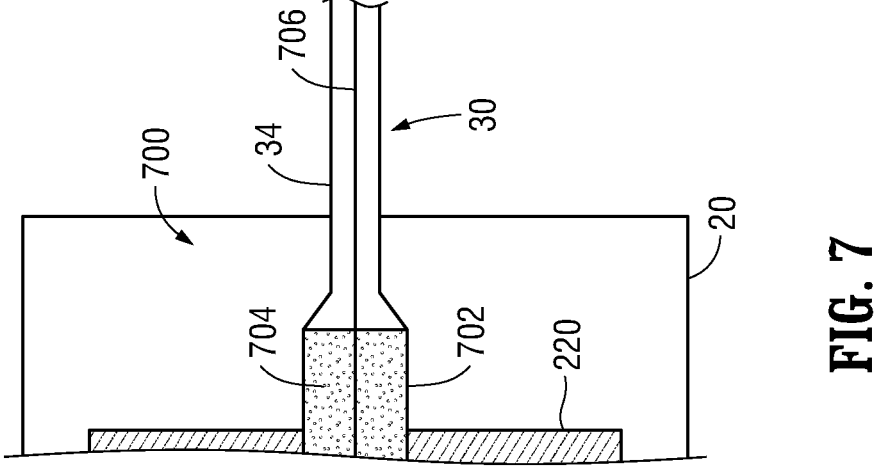
FIG. 7 is a longitudinal cross-sectional view of a proximal portion of a shaft configured for use with the surgical instrument of FIG. 1 including a seal in accordance with the present disclosure.

With reference to FIG. 7, a seal configuration 700 provided in accordance with the present disclosure is shown in use at location "A" (FIGS. 1, 2A-2C, and 6). More specifically, seal configuration 700 includes an enlarged proximal end portion 702 of proximal segment 34 of shaft 30 and a seal 704 disposed therein. Enlarged proximal end portion 702 is disposed within housing 20 and secured, e.g., welded or otherwise attached, to distal plate 220 of lead screw sub-assembly 210 (see FIGS. 2A-2C). Enlarged proximal end portion 702 defines a larger internal diameter as compared to the body of proximal segment 34 of shaft 30. The relatively larger internal diameter of enlarged proximal end portion 702 facilitates the manufacture of seal 704 and/or assembly of seal 704 within enlarged proximal end portion 702. Further, upon assembly, seal 704 is substantially retained in position within enlarged proximal end portion 702 of proximal segment 34 of shaft 30 as distal plate 220 inhibits substantial proximal movement of seal 704 while the smaller diameter body of proximal segment 34 of shaft 30 inhibits substantial distal movement of seal 704. Seal 704 may be formed as a solid piece of material, e.g., an elastomeric material, as a single piece of material that is inserted into enlarged proximal end portion 702 or multiple pieces of material coupled to one another before or during insertion into enlarged proximal end portion 702. In some configurations, seal 704 may include a greased or otherwise lubricated plug to facilitate insertion and formation of a seal. Grease or other lubrication may likewise be utilized to facilitate sealing with any of the other configurations detailed herein. Seal 704 may alternatively be a semi-solid material, e.g., a gel, or may be a material that is injected into enlarged proximal end portion 702 in one form, state, or condition before transitioning to another form, state, or condition e.g., foam, injectable silicone, etc. Combinations of the above may also be utilized. Regardless of the particular configuration of seal 704, seal 704 serves to establish a seal within enlarged proximal end portion 702 and about the actuation components 706 extending therethrough, e.g., articulation cables 38 (FIGS. 1, 4, and 5), knife tube 62 (FIGS. 4 and 5), and lead wires 99 (FIG. 1). Thus, seal 704 functions to inhibit the passage of fluids proximally across seal 704 while still enabling operation of the actuation components 706 extending therethrough. Other suitable configurations of seal 704 such as those detailed hereinbelow are also contemplated.

Figure 8:
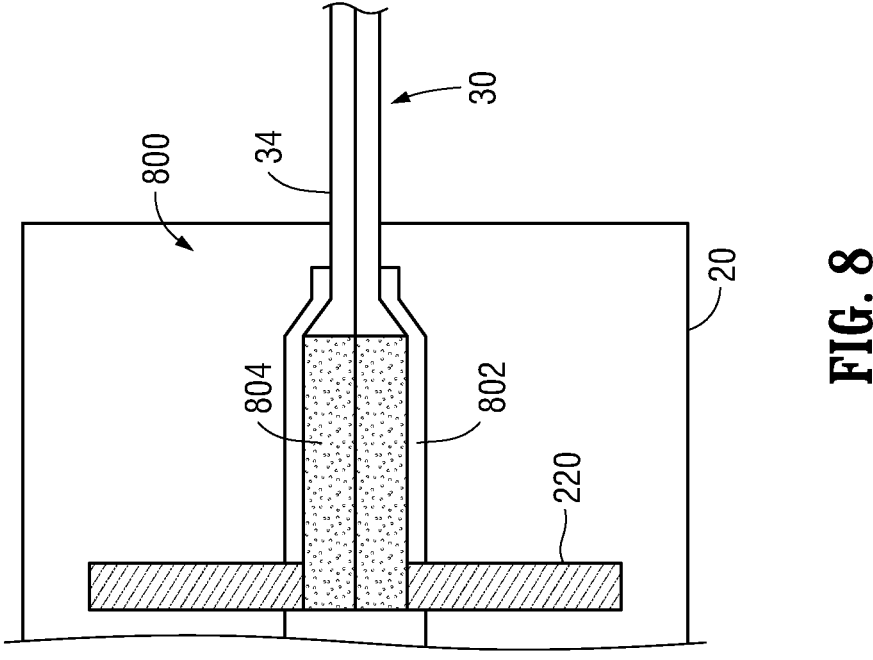
FIG. 8 is a longitudinal cross-sectional view of another proximal portion of a shaft configured for use with the surgical instrument of FIG. 1 including a seal in accordance with the present disclosure.

Referring to FIG. 8, another seal configuration 800 provided in accordance with the present disclosure is shown in use at location "A" (FIGS. 1, 2A-2C, and 6). More specifically, seal configuration 800 includes a connector shaft 802 including a seal 804 disposed therein. Connector shaft 802 is disposed within housing 20 and secured, e.g., welded or otherwise attached, to distal plate 220 of lead screw subassembly 210 (see FIGS. 2A-2C) and proximal segment 34 of shaft 30 to thereby secure proximal segment 34 of shaft 30 to distal plate 220. Connector shaft 802 defines a larger internal diameter as compared to proximal segment 34 of shaft 30. The relatively larger internal diameter of connector shaft 802 facilitates the manufacture of seal 804 and/or assembly of seal 704 within connector shaft 802. Further, upon assembly, seal 804 is substantially retained in position within connector shaft 802 proximal segment 34 of shaft 30 as distal plate 220 inhibits substantial proximal movement of seal 804 while the smaller diameter proximal segment 34 of shaft 30 inhibits substantial distal movement of seal 804. Seal 804 may be formed, inserted, assembled, and/or configured similarly as detailed above with respect to seal 704 (FIG. 7) or in any other suitable manner.

Figure 9A:
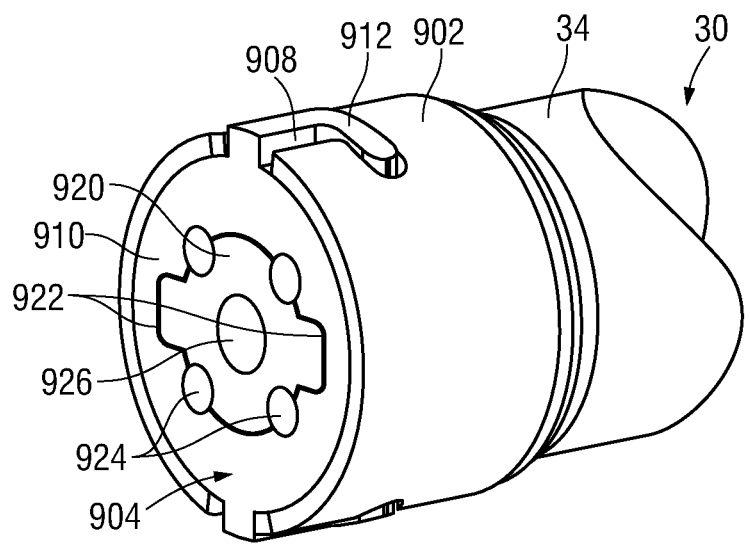
FIGS. 9A and 9B are perspective and exploded perspective views, respectively, of still another proximal portion of a shaft configured for use with the surgical instrument of FIG. 1 including a seal in accordance with the present disclosure.
Figure 9B:
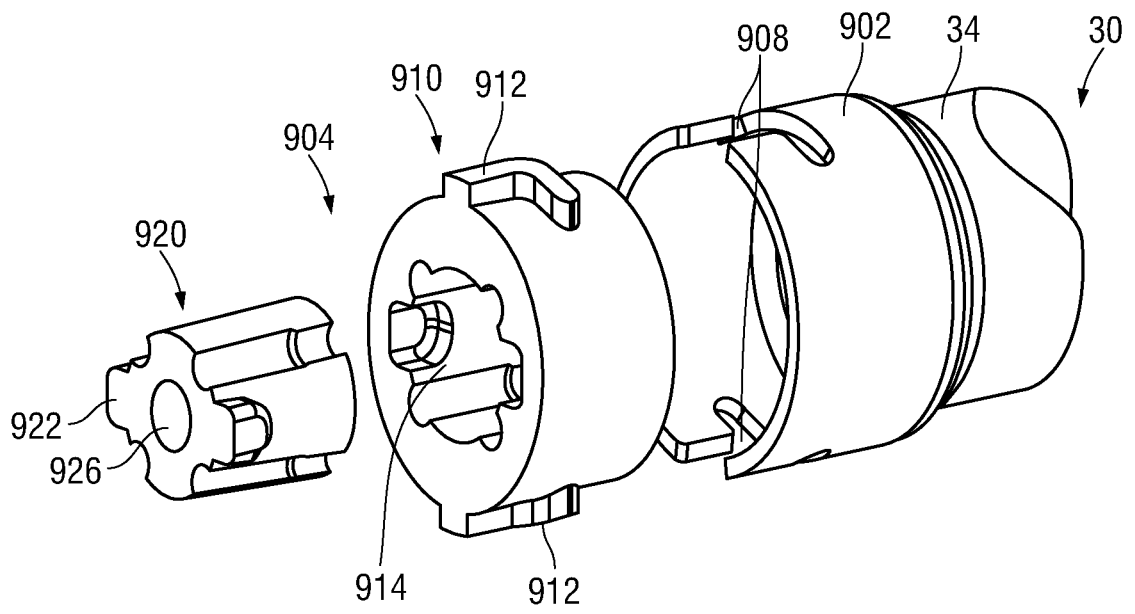

FIGS. 9A and 9B illustrate still another seal configuration 900 provided in accordance with the present disclosure for use at location "A" (FIGS. 1, 2A-2C, and 6) or any other suitable location. More specifically, seal configuration 900 includes an enlarged proximal end portion 902 of proximal segment 34 of shaft 30 and a two-part seal 904 disposed therein. Enlarged proximal end portion 902 is disposed within housing 20 (see FIGS. 4 and 5) and may be secured, e.g., welded or otherwise attached, to distal plate 220 of lead screw sub-assembly 210 (see FIGS. 2A-2C). Enlarged proximal end portion 902 defines a larger internal diameter as compared to the body of proximal segment 34 of shaft 30. The relatively larger internal diameter of enlarged proximal end portion 902 facilitates the manufacture of seal 904 and/or assembly of seal 904 within enlarged proximal end portion 902. Enlarged proximal end portion 902 includes one or more retention slots 908 defined therein, each defining an L-shaped configuration. Although two diametrically-opposed, L-shaped retention slots 908 are shown in FIG. 9B, other number and/or configuration of retention slots 908 are also contemplated such as, for example, T-shaped slots.

Two-part seal 904 includes an outer collar 910 and an inner plug 920. Outer collar 910 includes one or more retention protrusion 912 extending radially outwardly therefrom, each defining an L-shaped configuration. Although two diametrically-opposed, L-shaped protrusions 912 are shown in FIG. 9B, other number and/or configuration of retention protrusions 912 complementary to retention slots 908 are also contemplated. Retention protrusions 912 are configured for receipt within retention slots 908 to fixedly seat outer collar 910 within enlarged proximal end portion 902 in sealed relation against an inner annular surface thereof. Outer collar 910 further includes an irregular, e.g., non-circular, lumen 914 defined therethrough.

Inner plug 920 of seal 904 is configured for complementary receipt within irregular lumen 914 of outer collar 910. Outer collar 910 and inner plug 920, with inner plug 920 received within irregular lumen 914 of outer collar 910, define complementary features 922, e.g., protrusions and recesses, and/or other suitable features or configurations such that inner plug 920 is fixedly retained within outer collar 910 and forms a seal therewith (notwithstanding any defined passages therethrough). Outer collar 910 and inner plug 920 may also cooperate to define one or more radial lumens 924 therebetween and/or inner plug 920 may define a central lumen 926. Lumens 924, 926 are configured to establish a seal with actuation components extending therethrough, e.g., articulation cables 38 (FIGS. 1, 4, and 5), knife tube 62 (FIGS. 4 and 5), and lead wires 99 (FIG. 1).

Outer collar 910 and inner plug 920 of seal 904 may be formed from the same or different materials and are configured to cooperate to establish a seal within enlarged proximal end portion 902 and about the actuation components extending therethrough. Thus, seal 904 functions to inhibit the passage of fluids proximally across seal 904 while still enabling operation of the actuation components extending therethrough.

Turning to FIGS. 10-13, various seal configurations 1000, 1100, 1200, 1300 provided in accordance with the present disclosure are shown. Seal configurations 1000, 1100, 1200, 1300 may be utilized with or without an enlarged proximal end portion of proximal segment 34 of shaft 30 and include retention features defined on, within, or otherwise associated with a proximal end portion 1002, 1102, 1202, 1302 of proximal segment 34 of shaft 30 to facilitate maintaining the corresponding seals 1004, 1104, 1204, 1304 in sealing relation and substantially fixed position within proximal segment 34 of shaft 30. Seal configurations 1000, 1100, 1200, 1300 may be duplicated and/or used in combination with one another and, although described for use at location "A," may alternatively or additionally, to the extent consistent, be utilized at location "B" and/or any other suitable location(s) (see FIGS. 1, 2A-2C, and 6).

Figure 10:
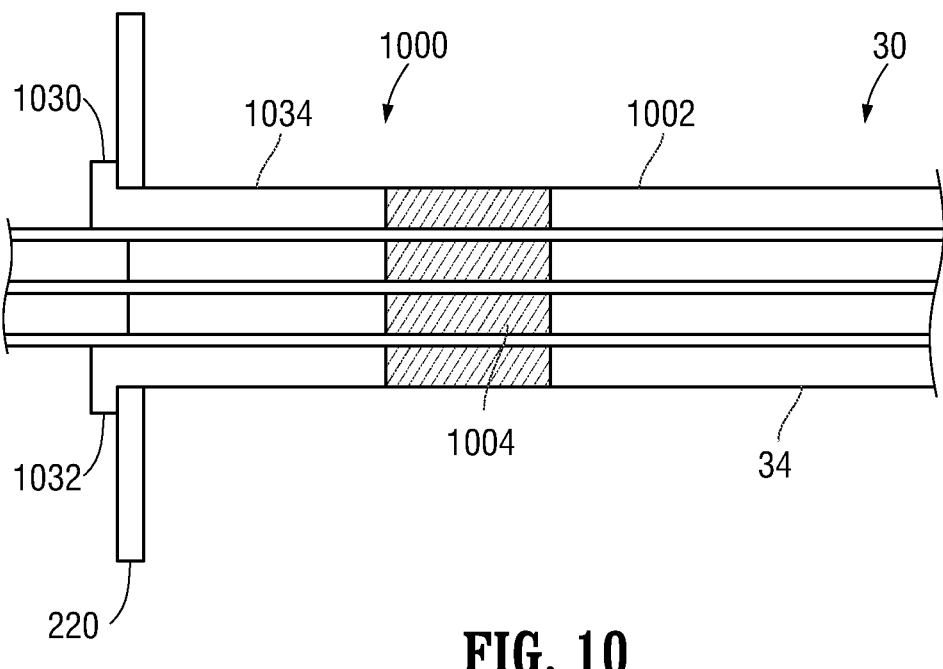
FIGS. 10-13 are longitudinal cross-sectional views of various proximal portions of shafts configured for use with the surgical instrument of FIG. 1 including seals in accordance with the present disclosure.

Seal configuration 1000 illustrated in FIG. 10 includes a lock ring 1030 having a proximal flange 1032 configured to proximally abut distal plate 220 of lead screw sub-assembly 210 (see FIGS. 2A-2C) and a distal body 1034 configured to extend through distal plate 220 and into proximal end portion 1002 of proximal segment 34 of shaft 30, e.g., in press-fit fashion. Distal body 1034 reduces the effective inner diameter of proximal end portion 1002, thus inhibiting proximal movement of seal 1004. Seal 1004 may be similar to seal 700 (FIG. 7) or any other suitable seal.

Figure 11:
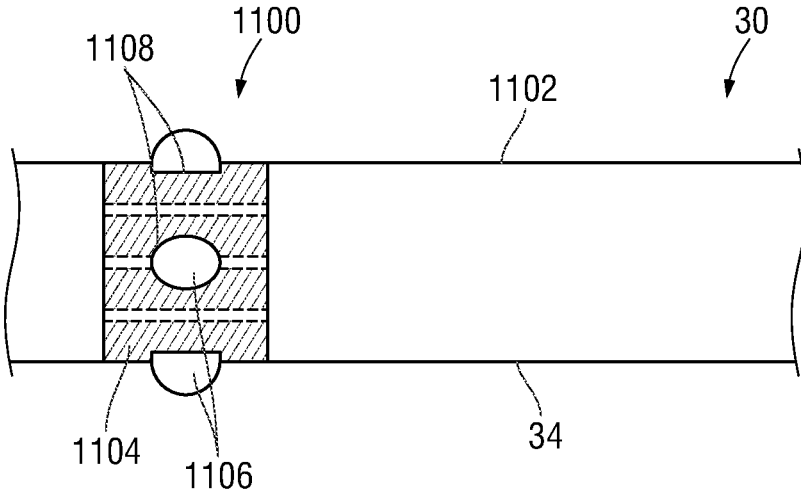

As illustrated in FIG. 11, seal configuration 1100 includes a plurality of protrusions 1106 disposed annularly about and extending radially outwardly from seal 1104 and a plurality of corresponding apertures 1108 defined annularly about proximal end portion 1102 of proximal segment 34 of shaft 30, although the opposite configuration or protrusions and apertures on both seal 1104 and proximal end portion 1102 are also contemplated. Upon insertion of seal 1104 into proximal end portion 1102, protrusions 1106 are compressed radially inwardly to enable insertion of seal 1104 into proximal end portion 1102. Upon alignment of protrusions 1106 with apertures 1108, protrusions 1106 are resiliently returned to extend through apertures 1108, thereby retaining seal 1104 in position within proximal end portion 1102. Seal 1104 may otherwise be similar to seal 700 (FIG. 7) or any other suitable seal.

Figure 12:
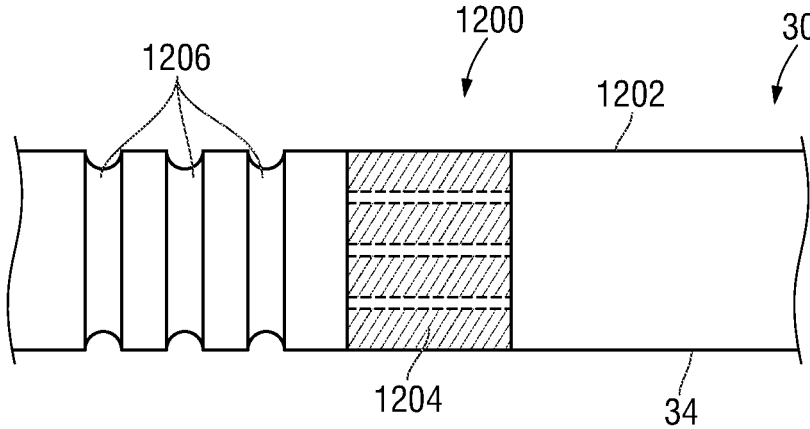

Seal configuration 1200 illustrated in FIG. 12 includes one or more annular ribs 1206 extending radially inwardly into proximal end portion 1202 of proximal segment 34 of shaft 30. Ribs 1206 may be formed via indenting the outer surface of proximal end portion 1202, adding additional material within proximal end portion 1202, or in any other suitable manner. Further, ribs 1206 may be disposed proximally, distally, or on both sides of seal 1204. Upon insertion of seal 1204 into proximal end portion 1202, seal 1204 is compressed radially inwardly to enable seal 1204 to pass through ribs 1206 to a position more-distal of ribs 1206. Once seal 1204 clears ribs 1206, seal 1204 is resiliently returned to seal against the inner surface proximal end portion 1202. The reduced effective diameter of proximal end portion 1202 provided by ribs 1206 inhibits seal 1204 from moving proximally. Seal 1204 may be similar to seal 700 (FIG. 7) or any other suitable seal.

Figure 13:
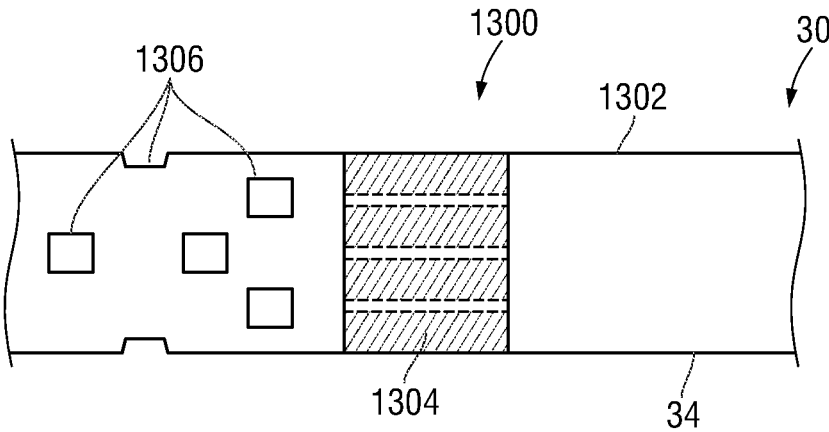

Illustrated in FIG. 13 is seal configuration 1300 which is similar to seal configuration 1200 (FIG. 12) except that, rather than ribs inhibiting proximal movement of the seal, seal configuration 1300 includes a plurality of radially and axially arranged protrusions 1306 protruding radially inwardly into the interior of proximal end portion 1302 to reduce the effective inner diameter thereof.

Figure 14:
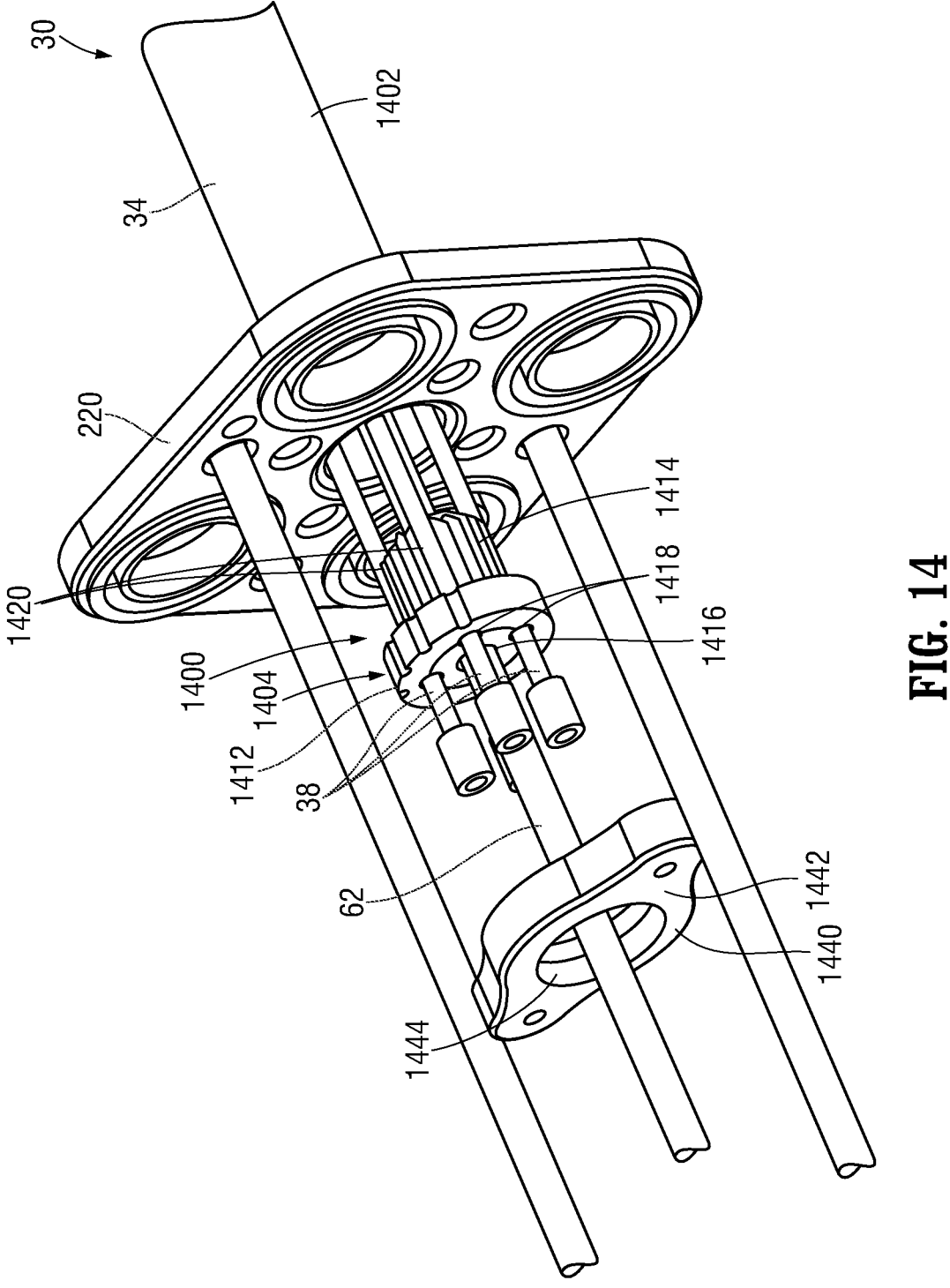
FIG. 14 is an exploded perspective view of a portion of an actuation assembly configured for use with the surgical instrument of FIG. 1, including a seal in accordance with the present disclosure.

Turning to FIG. 14, yet another seal configuration 1400 in accordance with the present disclosure is provided for use at location "A," location "C," a location therebetween, or any other suitable location(s) (sec FIGS. 1, 2A-2C, and 6). Seal configuration 1400 includes a seal 1404 and a lock plate 1440. Seal 1404 includes a proximal flange 1412 configured to proximally abut distal plate 220 and a distal body 1414 configured to extend through distal plate 220 and into proximal end portion 1402 of proximal segment 34 of shaft 30. Seal 1404 may include one or more lumens 1416 extending completely therethrough, one or more apertures 1418 extending through proximal flange 1412, and/or one or more channels 1420 extending along distal body 1414 that individually or in cooperation sealingly engage the actuation components extending therethrough, e.g., articulation cables 38, knife tube 62, and lead wires 99 (FIG. 1). Slits defined within proximal flange 1412 and/or distal body 1414 provide scalable connections between the lumens 1416, apertures 1418, and/or exterior annular surfaces of proximal flange 1412 and/or distal body 1414 to facilitate the insertion and engagement of the actuation components therein. Such slits may likewise be used for similar purposes in other seal configurations detailed herein.

Lock plate 1440 includes a body 1442 defining one or more apertures 1444 that align with the lumens, 1416, apertures 1418, and channels 1420 of seal 1404 to enable passage of the actuation components, e.g., articulation cables 38, knife tube 62, and lead wires 99 (FIG. 1), therethrough. Lock plate 1440 is configured to proximally abut proximal flange 1412 of seal 1404 to at least partially compress proximal flange 1412 between lock plate 1440 and distal plate 220, thereby establishing a seal about the passage extending through distal plate 220 and shaft 30. Alternatively or additionally, any gap(s) may be filled with grease or other suitable material to establish the seal. Lock plate 1440 is secured in position relative to distal plate 220, this maintaining the seal, via screwing lock plate 1440 onto distal plate 220 and/or using any other suitable fasteners or engagement features. Distal body 1414 of seal 1404 may additionally or alternatively extend through distal plate 220 and into proximal end portion 1402 of proximal segment 34 of shaft 30 in sealing relation with an inner surface of proximal end portion 1402 to establish a seal therein.

Referring to FIGS. 15-17A, still yet other configurations 1500, 1600, 1700 are provided in accordance with the present disclosure configured for use at location "A" and/or any other suitable location(s) (see FIGS. 1, 2A-2C, and 6). Configurations 1500, 1600, 1700 may each include one or more portions 1501, 1601, 1701 of housing 20 that are sealed off, e.g., via a bulkhead 1503, 1603 or other suitable structure or combination of structures, to define a sealed volume within housing 20; in some configurations, the entirely of the interior of housing 20 defines the sealed volume. Although portions 1501, 1601, 1701 are illustrated at the distal end of housing 20, additional and/or alternative locations are also contemplated.

Figure 15:
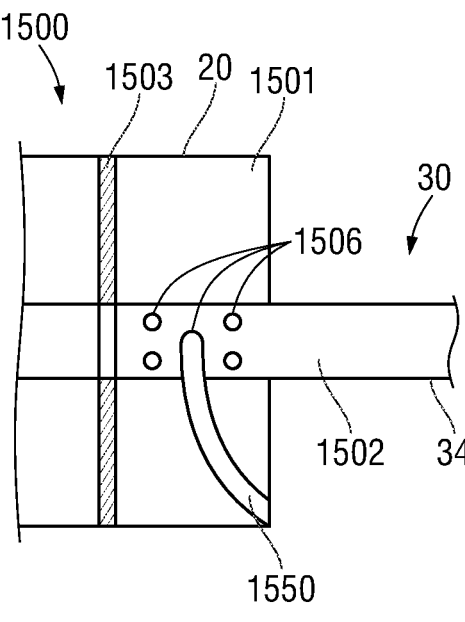
FIGS. 15, 16, and 17A are longitudinal cross-sectional views of distal portions of housings and proximal portions of shafts configured for use with the surgical instrument of FIG. 1 including various configurations for sealing, absorbing, and/or draining in accordance with the present disclosure.

With respect to configuration 1500 in FIG. 15, one or more apertures 1506 or other openings are defined through proximal end portion 1502 of proximal segment 34 of shaft 30 that fluidly communicate with the sealed volume defined by portion 1501. Thus, fluids traveling proximally through proximal segment 34 of shaft 30 and into housing 20 may exit proximal end portion 1502 and enter portion 1501 via apertures 1506. Alternatively or additionally, a drain tube 1550 connected to one of the apertures 1506 and/or in fluid communication with portion 1501 of housing 20 may be provided to enable drainage of such fluids. In such configuration, a fitting or other suitable connection (not shown) may be provided on housing 20 to enable connection of a drainage line (not shown).

Figure 16:
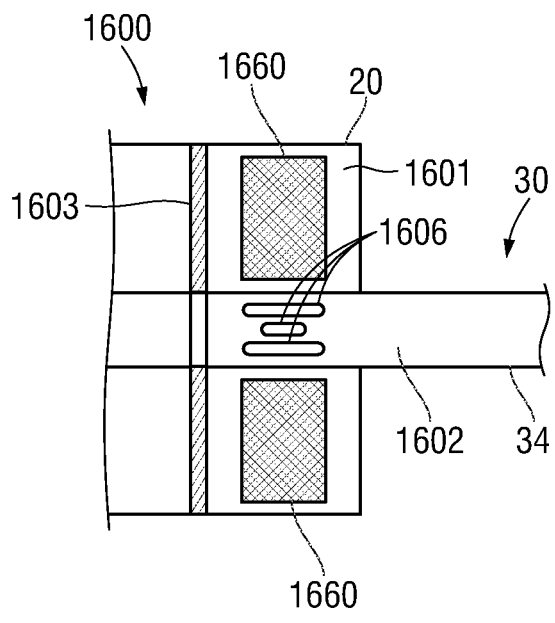

Configuration 1600 illustrated in FIG. 16 likewise includes one or more apertures 1606 or other openings are defined through proximal end portion 1602 of proximal segment 34 of shaft 30 that fluidly communicate with the sealed volume defined by portion 1601. Configuration 1600 difference from configuration 1500 (FIG. 15) in that, rather than providing a drain tube, configuration 1600 includes one or more sponges 1660 or other suitable fluid-absorbing materials disposed within portion 1601 so as to absorb fluids entering portion 1601 via apertures 1606.

Figure 17A:
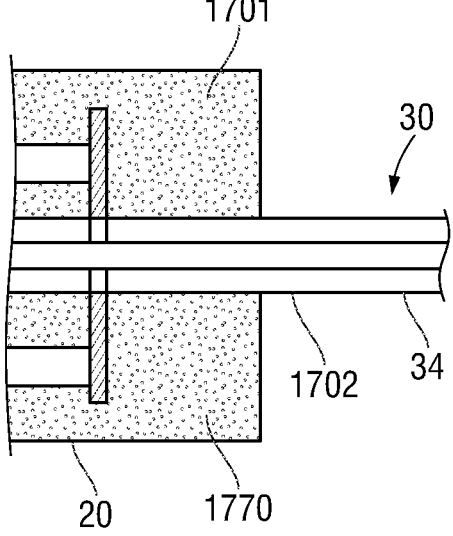
Figure 17B:
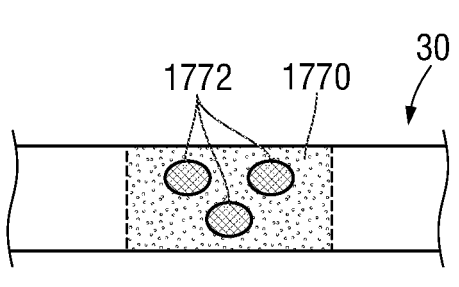
FIG. 17B is a longitudinal cross-sectional view of a portion of a shaft configured for use with the surgical instrument of FIG. 1 including still another seal in accordance with the present disclosure.

FIG. 17A illustrates a configuration 1700 wherein the portion 1701 of housing 20 or the entirety of housing 20 is filled with an injectable material 1770, e.g., a sealant material and/or absorbent material, to form a seal against passage fluids and/or to absorb fluids. The injectable material 1770 may be a foam, gel, grease, phase-change material, etc. As shown in FIG. 17B, in other configurations, apertures 1772 defined within shaft 30 (or other components) may be provided to enable injection of the injectable material 1770 to provide additional seals and/or absorbent areas, e.g., at locations "B" or "E" (see FIGS. 1, 2A-2C, and 6), e.g., sealing shaft 30 and the components extending therethrough.

Turning to FIG. 18, another seal 1804 provided in accordance with the present disclosure is configured for use at locations "A," "B," "E" (FIGS. 1, 2A-2C, and 6) and/or any other suitable location(s). Seal 1804 includes a pair of wedge seal members 1882, 1884. Wedge seal members 1882, 1884 may define complementary engagement features 1886, e.g., interlocking tabs, protrusion and apertures, etc., configured to engage one another to secure wedge seal members 1882, 1884 to one another. Each wedge seal member 1882, 1884 further defines one or more lumens 1888 extending therethrough that align with one another upon engagement of wedge seal members 1882, 1884. When wedge seal members 1882, 1884 are engaged with one another, seal 1804 may define a rectangular cross-sectional configuration, a circular cross-sectional configuration, or any other suitable configuration to enable sealing of seal 1804 within an area, e.g., within shaft 30 (FIG. 1). Lumens 1888 are configured to receive one or more actuation components, e.g., articulation cables 38 (FIGS. 1, 4, and 5), knife tube 62 (FIGS. 4 and 5), and lead wires 99 (FIG. 1), in sealing relation therewith while still enabling operation thereof.

In use with respect to shaft 30 (FIG. 1), for example, wedge seal member 1882 is inserted in a first direction, e.g., distally, through a portion of shaft 30 and about the one or more actuation components while wedge seal member 1884 is inserted in a second opposite direction, e.g., proximally, through a portion of shaft 30 and about the one or more actuation components until wedge seal members 1882, 1884 meet and engage one another via complementary engagement features 1886, thereby forming a seal within shaft 30 and about the one or more actuation components. Wedge seal members 1882, 1884 may be formed from the same or different materials including elastomeric materials or other suitable materials.

Referring to FIG. 19, another seal 1904 provided in accordance with the present disclosure is configured for use at locations "A," "B," "E" (FIGS. 1, 2A-2C, and 6) and/or any other suitable location(s). Seal 1904 includes a seal body 1920. Seal body 1920 is configured to establish a seal against an inner surface of a structure, e.g., an inner surface of shaft 30 (FIG. 1). Seal body 1920 has one or more lumens 1922 extending therethrough. Each lumen 1922 defines a diameter equal to or larger than a diameter of the actuation component(s), e.g., articulation cables 38 (FIGS. 1, 4, and 5), knife tube 62 (FIGS. 4 and 5), and lead wires 99 (FIG. 1), configured for passage therethrough. A plurality of duckbill seals 1924 extend from either or both sides of seal body 1920 with each duckbill seal 1924 surrounding an end of one of the lumens 1922. Duckbill seals 1924 may be zero-closure seals or may close to a diameter less than the actuation component(s), e.g., articulation cables 38 (FIGS. 1, 4, and 5), knife tube 62 (FIGS. 4 and 5), and lead wires 99 (FIG. 1), configured for passage therethrough. In this manner, seal body 1920 seals against the outer structure, e.g., shaft 30, while duckbill seals 1924 seal about the inner structure(s), e.g., the actuation component(s). Duckbill seals 1924 may additionally or alternatively establish a seal about the actuation component(s) when there is a pressure differential across seal 1904, e.g., when shaft 30 (FIG. 1) is inserted into an insufflated body cavity.

Turning to FIG. 20, another seal 2004 provided is configured for use at locations "A," "B," "E" (FIGS. 1, 2A-2C, and 6) and/or any other suitable location(s) and includes a compressible seal body 2006 captured between a pair of rigid plates 2008. Body 2006 and plates 2008 may cooperate to define lumens 2010 therethrough to enable passage of actuation components in sealed relation with seal body 2006. During assembly, seal body 2006 may be inserted into an outer structure, e.g., shaft 30, and/or about an inner structure, e.g., one or more actuation components, prior to positioning of plates 2008. Plates 2008 may then be positioned on either side of seal body 2006 and moved towards one another to axially compress seal body 2006, urging seal body 2006 to seal within the outer structure and/or about the inner structure. Plates 2008 may be retained in position via engagement with one another and/or the outer structure.

Figures 21, 22, 23, 24, 25:
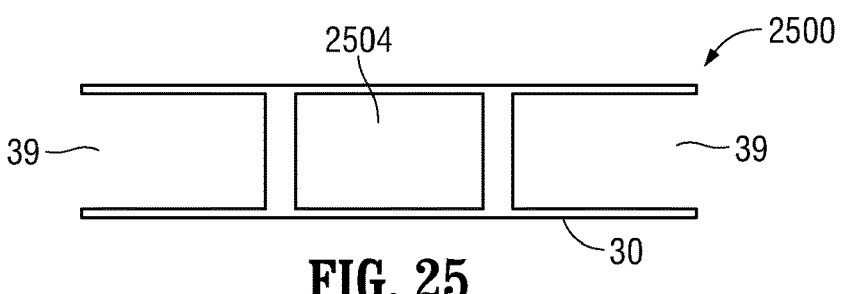
FIGS. 21 and 22 are transverse cross-sectional views of yet other seals in accordance with the present disclosure.
FIG. 23 is a transverse cross-sectional view of another seal in accordance with the present disclosure.
FIGS. 24 and 25 are longitudinal cross-sectional views of portion of shafts configured for use with the surgical instrument of FIG. 1 including other seals in accordance with the present disclosure.

With reference to FIG. 21, still yet another seal 2104 is configured for use at locations "A," "B," "E" (FIGS. 1, 2A-2C, and 6) and/or any other suitable location(s). Seal 2104 includes a plurality of seal components 2105 each sealed about and disposed in fixed relation, e.g., via over-molding, relative to an actuation component, e.g., one of the articulation cables 38. Seal components 2105 cooperate to act as wipers that maintain a seal about an outer structure, e.g., shaft 30, and/or an inner structure, e.g., knife tube 62, even where relative translation therebetween occurs.

Referring to FIG. 22, an absorbent and/or seal member 2204 provided in accordance with the present disclosure for use at locations "A," "B," "E" (FIGS. 1, 2A-2C, and 6) and/or any other suitable location(s) is initially disposed in a contracted configuration. Member 2204 is disposed, e.g., sealingly disposed, about an inner actuation component, e.g., knife tube 62, and may define a slit 2206 to enable transverse insertion of member 2204 about knife tube 62. Member 2204 is configured for positioning within shaft 30 (or other suitable outer component) and is initially disposed in non-sealing relation therewith, occupying a relatively small volume within shaft 30. Slit 2206 may be a zero-closure slit. As fluids contact and are absorbed by member 2204, member 2204 expands to fill a relatively larger volume within shaft 30 and, in some configurations, when sufficiently saturated and expanded, established a seal therein.

FIG. 23 illustrates another seal 2304 provided in accordance with the present disclosure for use at locations "A," "B," "E" (FIGS. 1, 2A-2C, and 6). For example, seal 2304 may be configured for positioning within an outer structure, e.g., shaft 30 (FIG. 1) to establish a seal about an inner surface thereof. Seal 2304 includes a central aperture 2306 and a plurality of radial apertures 2308. Apertures 2306, 2308 are configured to receive and sealingly engage actuation component(s), e.g., articulation cables 38 (FIGS. 1, 4, and 5), knife tube 62 (FIGS. 4 and 5), and lead wires 99 (FIG. 1). Each aperture 2306, 2308 includes a slit 2307, 2309, respectively, connecting the aperture 2306, 2308 with an outer annular periphery of seal 2304 such that each of the actuation components may be slid transversely through one of the slits 2307, 2309 and into sealing engagement within the corresponding aperture 2306, 2308, respectively. Slits 2307, 2309 may be zero-closure slits.

As shown in FIG. 24, another seal configuration 2400 is provided including a seal member 2404 defining one or more apertures 2406 extending longitudinally therethrough. Seal configuration 2400 may be used at locations "A," "B," "E" (FIGS. 1, 2A-2C, and 6) and/or any other suitable location(s). Seal member 2404 is configured for insertion into a structure and to establish a seal against an inner surface of the structure, e.g., an inner surface of shaft 30 (FIG. 1). The one or more apertures 2406 may be configured to receive an actuation component(s), e.g., articulation cables 38 (FIGS. 1, 4, and 5), knife tube 62 (FIGS. 4 and 5), and lead wires 99 (FIG. 1). A portion of seal member 2404 is compressed radially inwardly, e.g., via a band 2420 disposed about a portion of seal member 2404, such that the one or more apertures 2406 are collapsed and seal member 2404 establishes a sealed engagement with the actuation component(s). While the compressed portion of seal member 2404 is no longer sufficiently expanded to seal shaft 30 (FIG. 1), other portions of seal member 2404 or another seal may be utilized to seal shaft 30 (FIG. 1).

FIG. 25 provides a seal configuration 2500 including a seal member 2504 similar to seal member 2404 (FIG. 24) except that, rather than radial inward compression, seal member 2504 may be configured to compress axially inwardly from opposed ends, e.g., via compression of seal member 2504 between two guide structures 39 disposed within shaft 30, to establish a seal within shaft 30 and/or about actuation component(s). Alternatively, seal member 2504 may be configured to any other seal detailed herein, e.g., seal 2304 (FIG. 2) and retained in substantially fixed position within shaft 30 between the guide structures 39 (with or without compression).

Figures 26A, 26B, 27, 28:
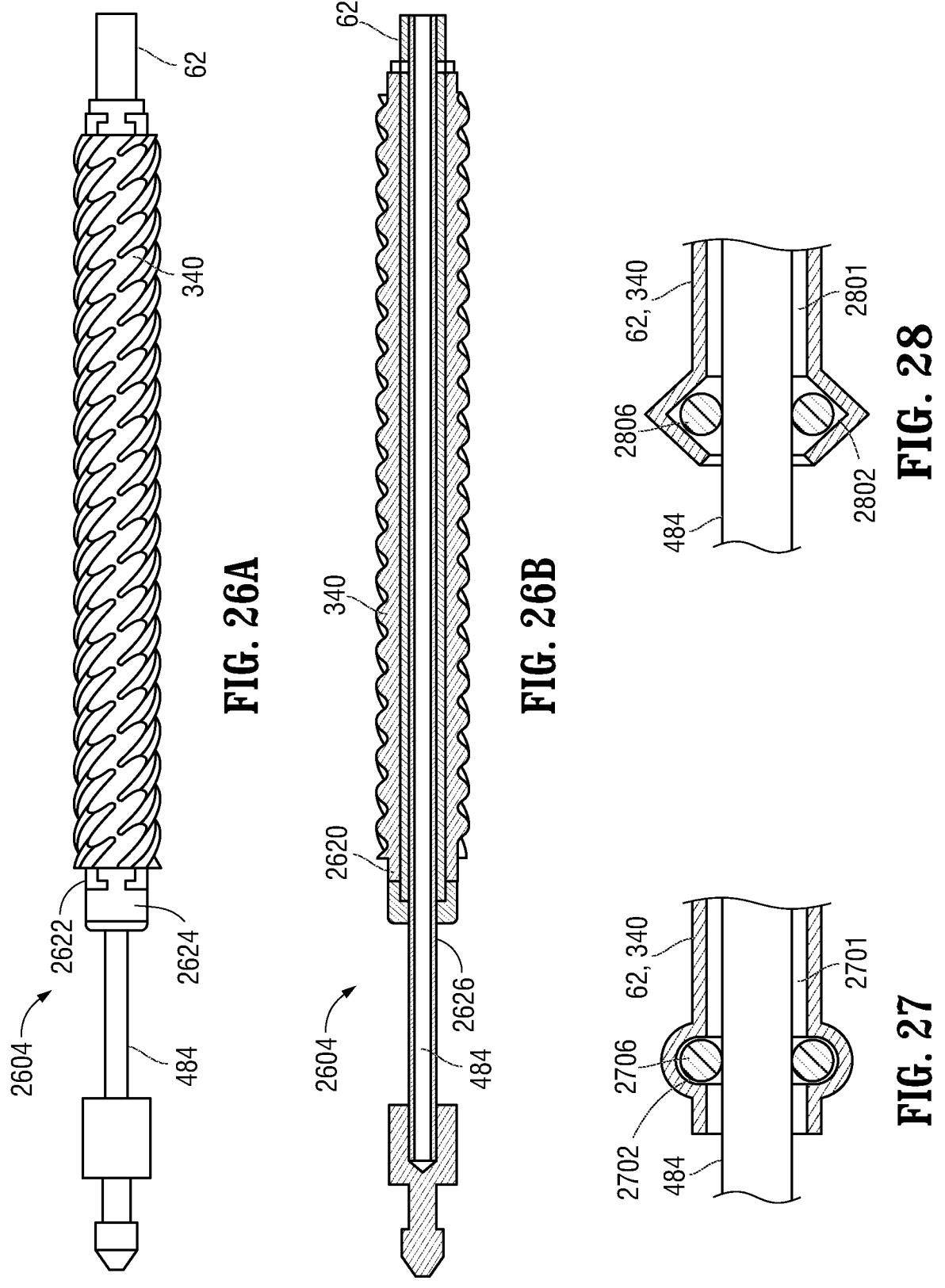
FIGS. 26A and 26B are side and longitudinal cross-sectional views, respectively, of a proximal portion of knife drive and jaw drive assemblies configured for use with the surgical instrument of FIG. 1 including seals in accordance with the present disclosure.
FIGS. 27 and 28 are longitudinal cross-sectional views of proximal portions of knife drive and jaw drive assemblies configured for use with the surgical instrument of FIG. 1 including seals in accordance with the present disclosure.

Turning to FIGS. 26A and 26B, as noted above, one or more seals may be provided at location "C" at or near proximal end portions of knife assembly 60, knife drive assembly 300, and/or jaw drive assembly 400 (sec FIGS. 2A-2C). More specifically, a seal 2604 may be provided to seal the annular area between knife drive lead screw 340 (and/or knife tube 62) and jaw drive rod 484.

Knife drive lead screw 340 may include a pair of diametrically opposed T-slots 2622 defined within an unthreaded proximal sleeve portion 2620 thereof. Seal 2604 may define a pair of diametrically opposed T-protrusions 2624 extending therefrom and configured for complementary engagement within the T-slots 2622 to engage seal 2604 with knife drive lead screw 340. Seal 2604 functions as a cap to sealingly enclose the open proximal ends of knife drive lead screw 340 and knife tube 62 disposed therein, with the exception of an aperture 2626 defined through a proximal wall thereof that sealingly receives jaw drive rod 484. Thus, fluids travelling proximally through knife tube 62 are inhibited from passing proximally beyond seal 2604.

FIGS. 27 and 28 illustrate alternative sealing arrangements for sealing between an inner component, e.g., jaw drive rod 484, and an outer component, e.g., knife tube 62 or knife drive lead screw 340, such as, for example, at location "C" at or near proximal end portions of knife assembly 60, knife drive assembly 300, and/or jaw drive assembly 400 (see FIGS. 2A-2C). An end of the outer component 62, 340 is formed with an internal annular pocket 2702, 2802 surrounding the lumen 2701, 2801 extending therethrough, e.g., via machining. The pocket 2702, 2802 may be semi-circular as shown with respect to pocket 2702, may be V-shaped as shown with respect to pocket 2802, or may define any other suitable configuration that enables capture of an O-ring 2706, 2806 therein. O-rings 2706, 2806 protrude into lumens 2701, 2801, respectively, to sealingly engage the inner component, e.g., jaw drive rod 484 extending through lumen 2701, 2801.

Figure 29A:
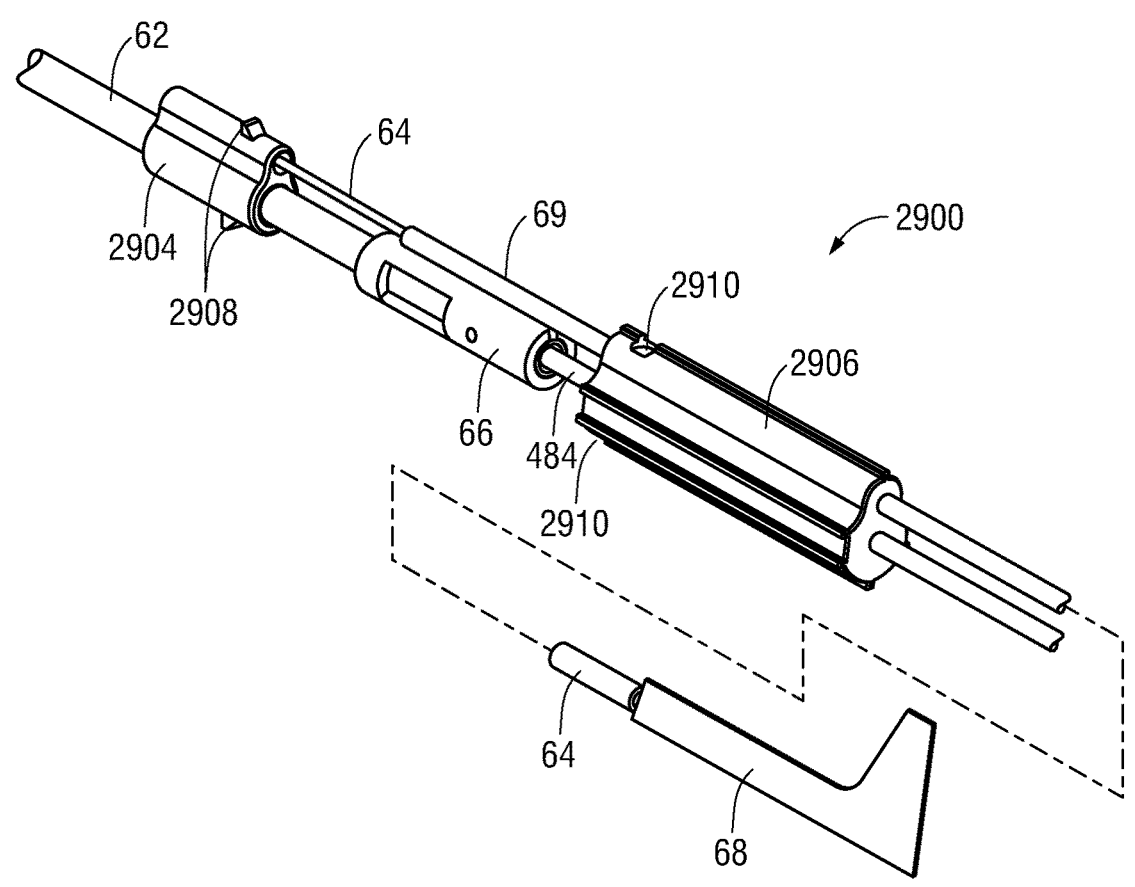
FIGS. 29A and 29B are exploded perspective and perspective views, respectively, of a distal portion of a knife assembly configured for use with the surgical instrument of FIG. 1 including still yet another seal in accordance with the present disclosure.
Figure 29B:
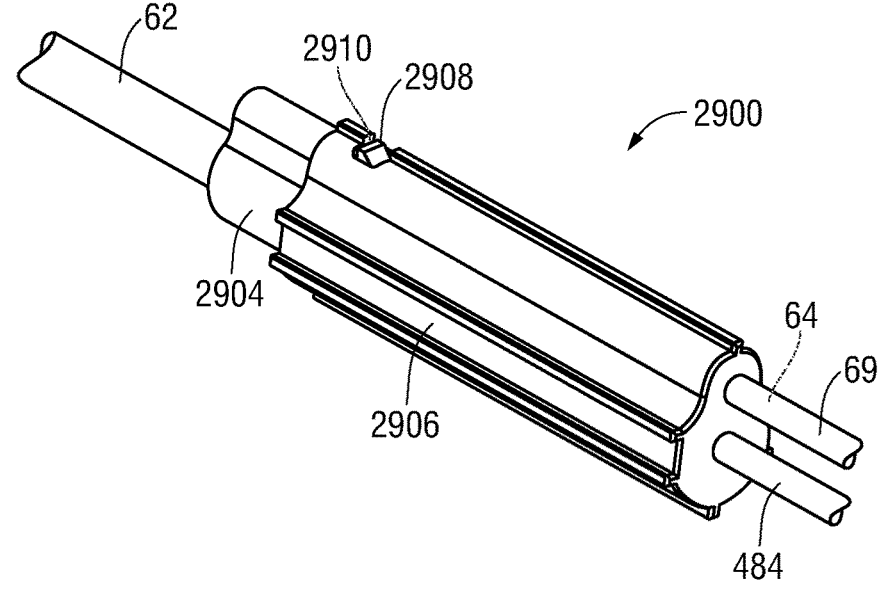

With reference to FIGS. 29A and 29B, a seal configuration 2900 is provided for establishing a seal at location "D," at or near distal end portions of knife assembly 60 and/or jaw drive assembly 400, although other locations are also contemplated (sec FIGS. 1-6). More specifically, by sealing the open distal end of knife tube 62 about jaw drive rod 484 extending therefrom with seal configuration 2900, fluids are inhibited from entering and traveling proximally through knife tube 62.

Referring also reference to FIG. 1, momentarily, knife tube 62 extends through housing 20 and proximal segment 34 of shaft 30 to a position proximally adjacent articulating section 36 of shaft 30 (see FIG. 1) wherein intermediate elongated collar 66 is engaged about the distal end portion of knife tube 62. Distal knife rod 64 is engaged to intermediate elongated collar 66, e.g., via a crimp tube 69, in an offset position and extends distally therefrom through articulating section 36 of shaft 30 to end effector assembly 40 (see FIG. 1) wherein knife blade 68 is engaged to distal knife rod 64, distally of articulating section 36 of shaft 30. Distal knife rod 64 is flexible and/or includes one or more joints or articulating portions to permit articulation of articulating section 36 of shaft 30 with distal knife rod 64 extending therethrough. Jaw drive rod 484 extends through and distally from knife tube 62, through articulating section 36 of shaft 30 to end effector assembly 40 (see FIG. 1) wherein jaw drive rod 484 operably couples with cam-slot assembly 52 including to enable pivoting of jaw member 42 relative to jaw member 44 and distal segment 32 of shaft 30 between a spaced-apart position (e.g., an open position of end effector assembly 40) and an approximated position (e.g. a closed position of end effector assembly 40) in response to translation of jaw drive rod 484. The offset engagement of distal knife rod 64 with intermediate collar 66 allows jaw drive rod 484 to extend distally from knife tube 62 to end effector assembly 40. Jaw drive rod 484 is flexible and/or includes one or more joints or articulating portions to permit articulation of articulating section 36 of shaft 30 with jaw drive rod 484 extending therethrough.

Referring again to FIGS. 29A and 29B, seal configuration 2900 includes a proximal seal member 2904 and a distal seal member 2906. Proximal seal 2904 is disposed about knife tube 62 proximally of intermediate elongated collar 66 and may also receive a proximal end portion of distal knife rod 64 therein. Distal seal 2906 is disposed about crimp tube 69 (which includes distal knife rod 64 extending therethrough) or directly about knife rod 64 (for example, in configurations where crimp tube 69 is omitted or otherwise positioned). Distal seal 2906 is also disposed about jaw drive rod 484 and is positioned distally of intermediate elongated collar 66.

Proximal and distal seals 2904, 2906 are configured to slide towards one another and about intermediate elongated collar 66 to a partially-overlapping condition wherein one of the seals, e.g., proximal seal 2904, is partially received within the other seal, e.g., distal seal 2906. Further, proximal and distal seals 2904, 2906 include complementary engagement features, e.g., lock tabs 2908 extending from the inner seal, e.g., proximal seal 2904, and lock apertures 2910 defined within the outer seal, e.g., distal seal 2906. In this manner, as proximal and distal seals 2904, 2906 are moved to the partially-overlapping condition, lock tabs 2908 are engaged within lock apertures 2910 to second proximal and distal seals 2904, 2906 with one another, collectively establishing a seal about intermediate elongated collar 66, the open distal end of knife tube 62, and jaw drive rod 484. Seal configuration 2900 may move together with knife tube 62 and/or may allow translation of jaw drive rod 484 relative thereto. Further, proximal and distal seals 2904, 2906 may be formed from the same or different materials.

Figure 30A:
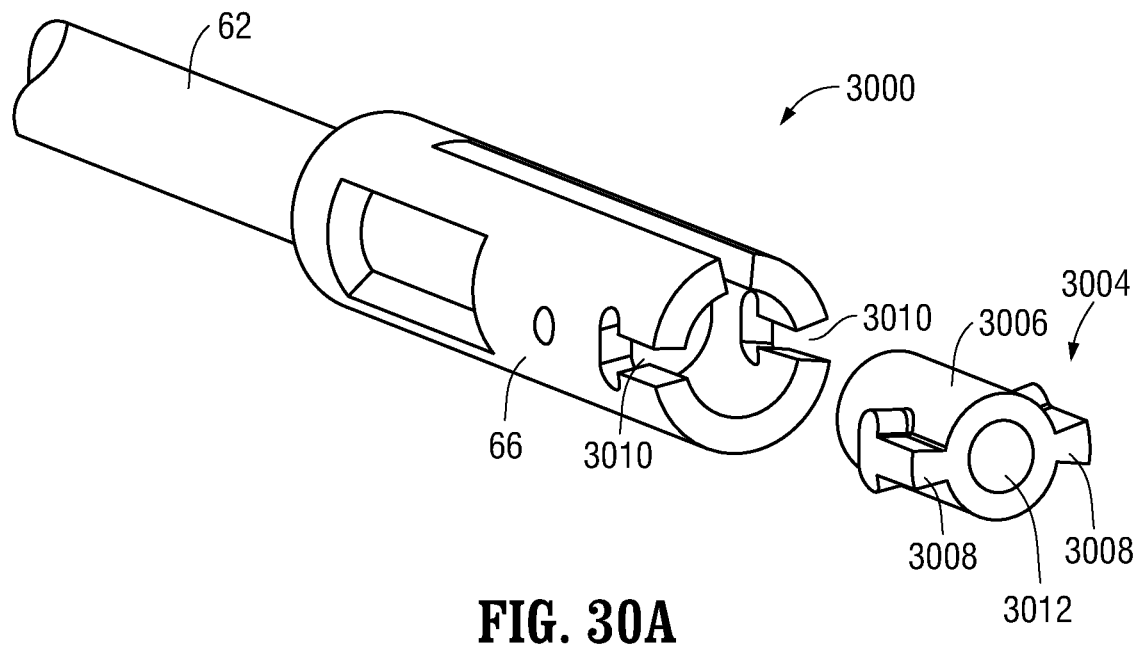
FIGS. 30A and 30B are exploded perspective and perspective views, respectively, of a portion of another knife assembly configured for use with the surgical instrument of FIG. 1 including a seal in accordance with the present disclosure.
Figure 30B:
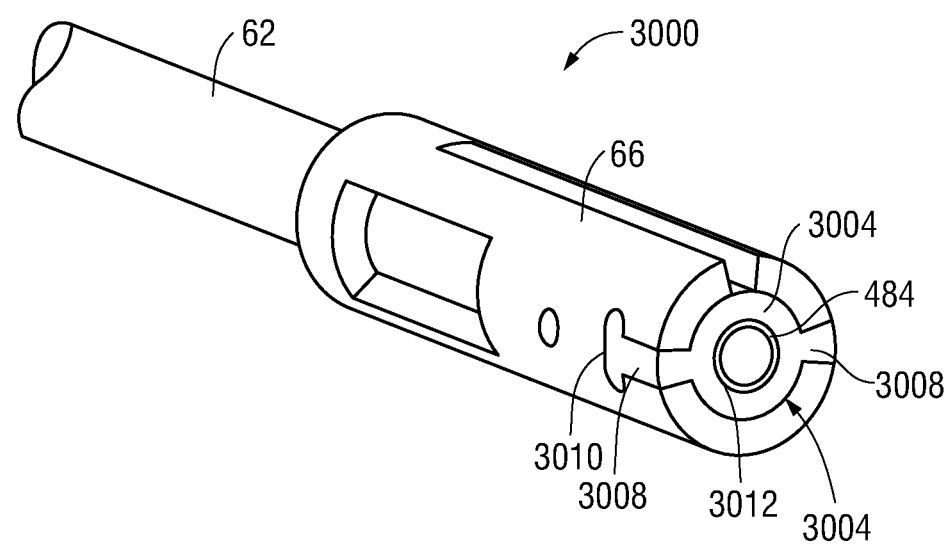

FIGS. 30A and 30B illustrate another seal configuration 3000 provided for establishing a seal at location "D," at or near distal end portions of knife assembly 60 and/or jaw drive assembly 400, although other locations are also contemplated (see FIGS. 1-6). Seal configuration 3000 is configured to seal the annular area defined between the open distal end of intermediate elongated collar 66 (and/or the open distal end of knife tube 62) and jaw drive rod 484.

Seal configuration 3000 includes a plug 3004 including a body 3006 configured to establish a seal about the inner surface of intermediate elongated collar 66 when inserted therein. Plug 3004 further includes a pair of diametrically opposed wings 3008 each defining a T-shaped configuration. Wings 3008 are configured for receipt within complementary diametrically opposed T-shaped slots 3010 defined within a distal end portion of intermediate elongated collar 66. Plug 3004 is inserted into intermediate elongated collar 66 such that body 3006 seals against the inner surface of intermediate elongated collar 66 while wings 3008 are engaged within slots 3010 to fixedly retain plug 3004 in sealing engagement within intermediate elongated collar 66. Plug 3004 further includes a central lumen 3012 extending therethrough that is configured to sealingly engage jaw drive rod 484 (FIG. 30B) while still allowing relative translation thereof. Plug 3004 may be formed from an elastomeric material or other suitable material.

Figure 31A:
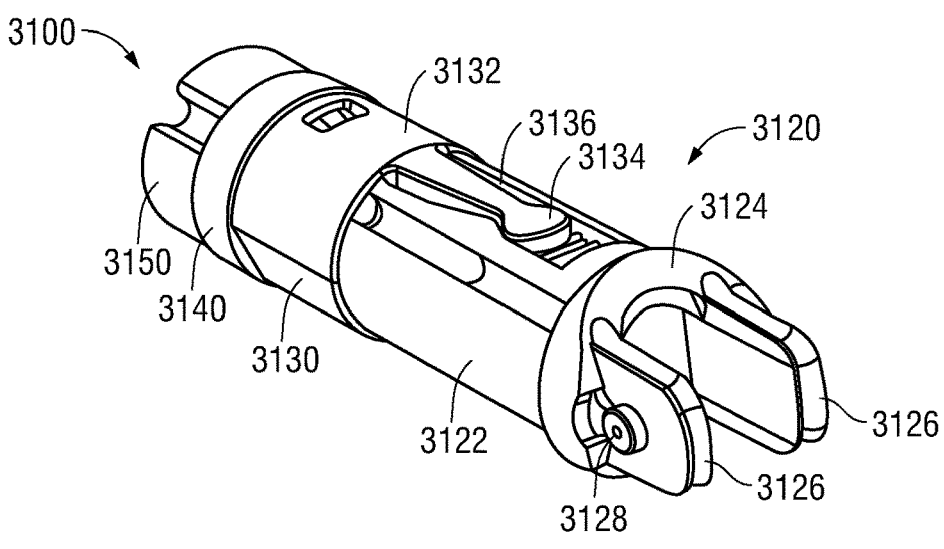
FIGS. 31A-31C are perspective, longitudinal cross-sectional, and end views respectively, of a portion of an articulating section configured for use with the surgical instrument of FIG. 1 including yet another seal in accordance with the present disclosure.

Turning to FIGS. 31A-13C, another seal configuration 3100 provided for establishing a seal at location "E," at or near articulating section 36 of shaft 30 (see also FIG. 1) is shown. Shaft 30, more specifically, includes articulating section 36 having one or more articulating components 37 (see FIG. 1). For example, one of the articulating components 37 (FIG. 1) may be a proximal link 3120 including a proximal body portion 3122, a distal face 3124 disposed at a distal end of proximal body portion 3122, and a pair of spaced-apart pivot flags 3126 extending distally from distal face 3124. Pivot flags 3126 include bosses 3128 to enable pivotable connection of proximal link 3120 with another articulating component 37 of articulating section 36 of shaft 30 (see FIG. 1). Proximal body portion 3122 may be configured for insertion into proximal segment 34 of shaft 30 with distal face 3124 abutting the open distal end of proximal segment 34 of shaft 30 (see FIG. 1).

Figure 31B:
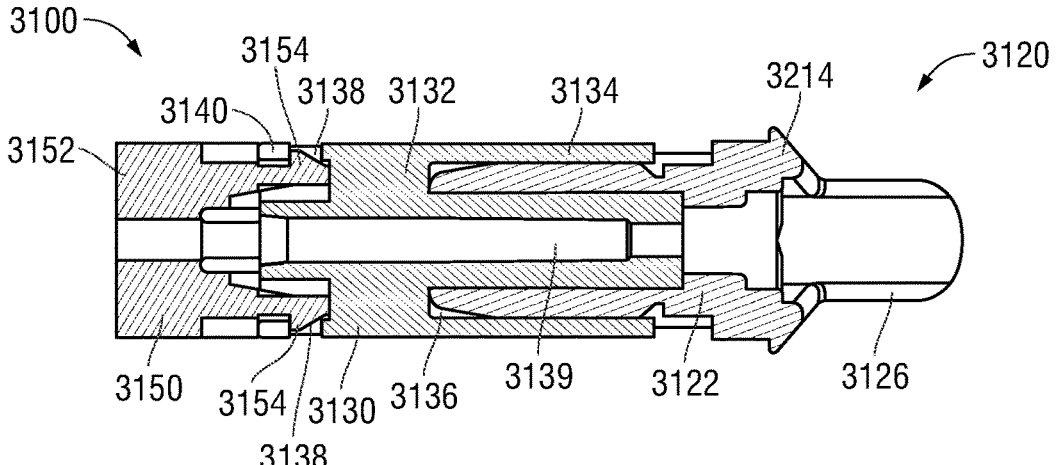
Figure 31C:
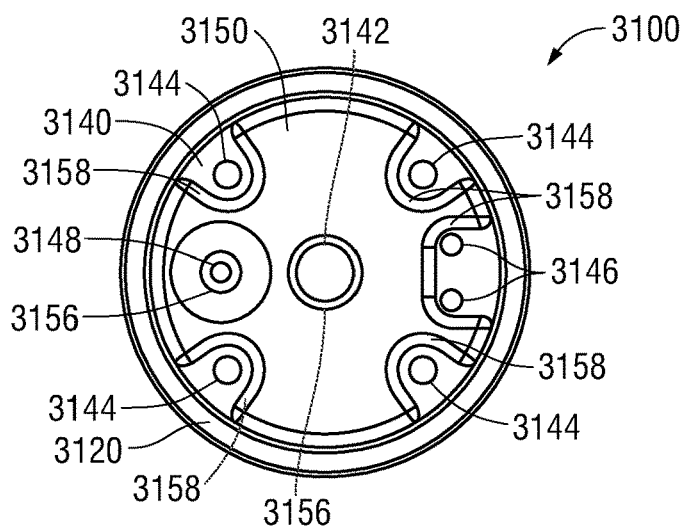

Continuing with reference to FIGS. 31A-31C, seal configuration 3100 includes a plug 3130, a seal ring 3140, and a clip 3150. Seal ring 3140 may be formed an elastomeric or other suitable material; plug 3130 and clip 3150 may be formed from elastomeric materials or from more rigid materials. Plug 3130 includes a base 3132 configured to proximally abut proximal body portion 3122 of proximal link 3120 and a pair of opposed arms 3134 extending distally from base 3132. Arms 3134 are configured for engagement within corresponding slots 3136 defined within proximal body portion 3122 of proximal link 3120. Seal ring 3140 is configured to proximally abut base 3132 of plug 3130 and clip 3150 includes a base 3152 configured to proximally abut seal ring 3140 and arms 3154 extending through seal ring 3150 and configured to engage, e.g., in snap-fit manner, slots 3138 of base 3132 of plug 3130 to thereby secure seal 3130 and clip 3150 with one another with seal ring 3140 disposed therebetween.

In the assembled condition, plug 3130, seal ring 3140, and clip 3150 cooperate with one another and proximal body portion 3122 of proximal link 3120 to establish a seal within the inner surface of proximal segment 34 of shaft 30 (see FIG. 1), e.g., via an outer annular surface of seal ring 3140, and to seal and guide the actuation components extending through proximal segment 34 of shaft 30 (see FIG. 1). More specifically, seal ring 3140 defines: a central aperture 3142 configured to sealingly receive jaw drive rod 484 (FIG. 2C); a plurality, e.g., four (4), radially-arranged apertures 3144 configured to sealingly receive articulation cables 38 (FIG. 1); a pair of adjacent apertures 3146 configured to sealingly receive the lead wires 99 (FIG. 1); and an offset aperture 3148 configured to sealingly receive distal knife rod 64 or crimp tube 69 disposed thereabout (see FIG. 29A). Clip 3150 may define apertures 3156 and/or cut-outs 3158 to provide access to the various apertures 3142-3148 defined through seal ring 3140. Plug 3130 may likewise include passages 3139, e.g., apertures and/or channels, for passage of the actuation components therethrough.

Figure 32:
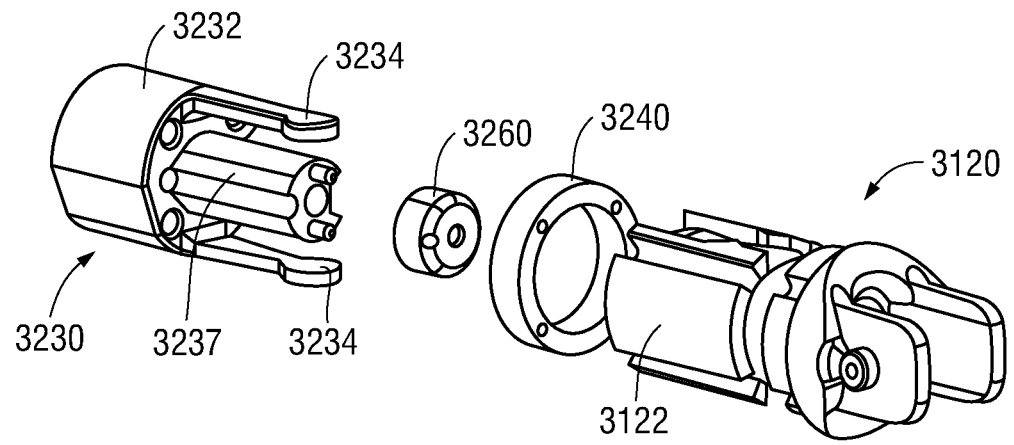
FIG. 32 is an exploded perspective view of another portion of an articulating section configured for use with the surgical instrument of FIG. 1 including a seal.

FIG. 32 illustrates still another seal configuration 3200 similar to seal configuration 3100 (FIGS. 31A-31C) and configured for operable engagement with proximal body portion 3122 of proximal link 3120 to establish a seal at location "E," at or near articulating section 36 of shaft 30 (see also FIG. 1). Seal configuration 3200 includes an engagement plug 3230, an outer seal ring 3240, and an inner seal plug 3260. Seal ring 3240 and seal plug 3260 may be formed from elastomeric or other suitable materials; engagement plug 3230 may be formed from an elastomeric material or from a more rigid material. Engagement plug 3230 includes a base 3232, a pair of opposed arms 3234 extending distally from base 3232, and a central cylinder 3237 extending distally from base 3232 between arms 3234. Outer seal ring 3240 is configured for positioning about central cylinder 3237 and between arms 3234 while inner seal plug 3260 is configured for distally abutting a distal end portion of central cylinder 3237. Engagement plug 3230 is configured to engage proximal body portion 3122 of proximal link 3120, e.g., via engagement of arms 3234 within slots similarly as detailed above with respect to seal configuration 3100 (FIGS. 31A-31C), with seal ring 3240 disposed therebetween in sealing engagement therewith, and with central cylinder 3237 and seal plug 3260 extending into proximal body portion 3122 of proximal link 3120 in sealing engagement therewith to form a seal against an inner surface of proximal link 3120. In use, outer seal ring 3240 establishes a seal within the inner surface of proximal segment 34 of shaft 30 (see FIG. 1) and seals about articulation cables 38 (FIG. 1) while inner seal plug 3260 seals about jaw drive rod 484 (FIG. 2C), the lead wires 99 (FIG. 1), and distal knife rod 64 (see FIG. 29A).

Figure 33:
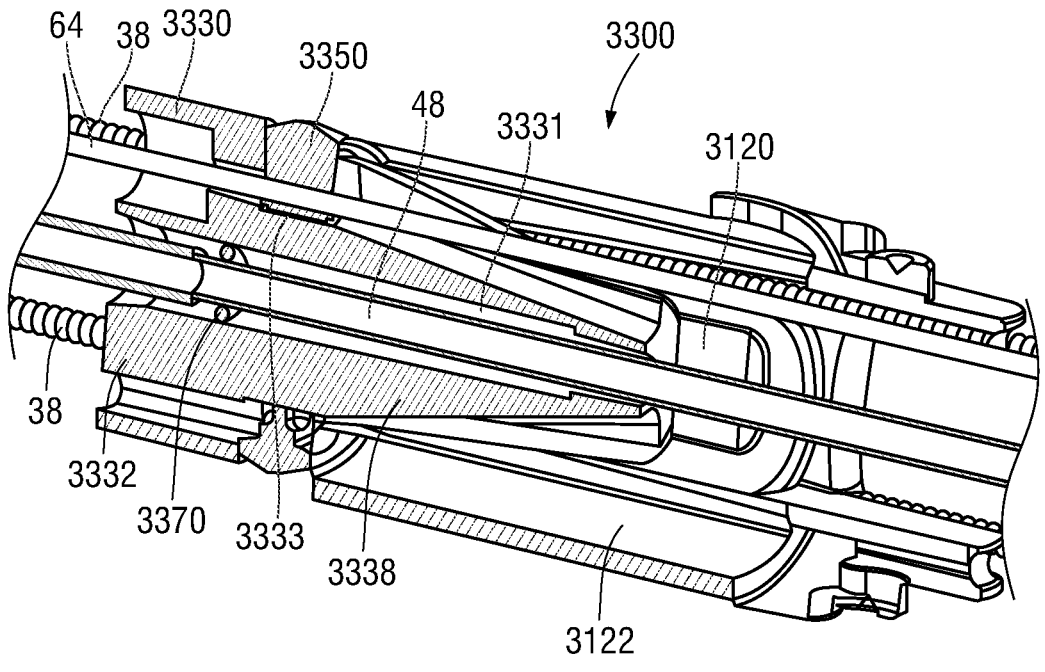
FIG. 33 is a longitudinal cross-sectional view of another portion of an articulating section configured for use with the surgical instrument of FIG. 1 including still another seal in accordance with the present disclosure.

Referring to FIG. 33, still another seal configuration 3300 similar to seal configurations 3100, 3200 (FIGS. 31A-31C and 32, respectively) configured for operable engagement with proximal body portion 3122 of proximal link 3120 to establish a seal at location "E," at or near articulating section 36 of shaft 30 (see also FIG. 1), is provided.

Seal configuration 3300 includes a plug 3330, an outer seal ring 3350, and an O-ring seal 3370. Plug 3330 includes a base 3332 and a conical body 3338 extending distally from base 3332. Conical body 3338 is configured for insertion into proximal body portion 3122 of proximal link 3120. Plug 3330 may be configured to engage proximal body portion 3122 in any suitable manner, e.g., press-fit, via arm and slot engagement, etc. Outer seal ring 3350 is configured for engagement within a slot 3333 defined within plug 3330 between base 3332 and conical body 3338 thereof. Outer seal ring 3350 protrudes radially outwardly from plug 3330 and proximal body portion 3122 of proximal link 3120 to enable formation of seal within the inner surface of proximal segment 34 of shaft 30 (see FIG. 1). Outer seal ring 3350 further defines radial lumens to sealingly engage articulation cables 38 and distal knife rod 64 or crimp tube 69 (see FIG. 29A). O-ring seal 3370 is disposed within central lumen 3331 of plug and is configured to seal jaw drive rod 484.

FIGS. 34-40 show various mechanisms for manually actuating the end effector assembly 40 (e.g., jaw members 42, 44) for inspection, cleaning and sterilization or for loading various hardware onto the end effector assembly 40 for use during an operation. It is contemplated that one or more of the below-described mechanisms and features may be applied to other aspects of the surgical instrument 10 depending upon a particular purpose and to allow manual actuation thereof.

Each of the below figures briefly describes the actuation of the end effector assembly 40 in relation to its respective manual actuation features. A more detailed explanation of the robot-assisted actuation of the end effector assembly 40 is describe above and, as such, only those details necessary for a complete understanding of the manual actuation components are described herein.

Figure 34:
FIG. 34 is a perspective, cut-away showing the various internal components of the jaw drive assembly and relative movements thereof.

FIG. 34 is an internal cross section of the various jaw actuation components described generally in detail above showing one general procedure for manually actuating the end effector assembly 40 utilizing one or more of the above-described designs. More particularly, jaw actuation assembly 4020 includes a compression assembly 4055 configured to house the spring force assembly 4050 and the jaw drive assembly 4005 including the jaw input gear 4022 operably coupled to the jaw drive input 4035. Spring force assembly 4050 includes a distal hub 4054, a proximal hub 4052, a drive gear 4030 and a locking tab 4075. Each hub 4052, 4054 includes an inner peripheral surface having a plurality of teeth 4053, 4057, respectively, configured to matingly engage a corresponding plurality of teeth or threads 4031 of the drive gear 4030.

Manual actuation of the jaw drive input 4035 rotates jaw input gear 4022 which couples to drive gear 4030. Rotation of the drive gear 4030 forces the proximal hub 4052 of the spring force assembly 4050 to linearly translate against the bias of the compression spring 4056 relative to the distal hub 4054 which, in turn, linearly translates the jaw drive rod 4084 by virtue of the mechanical engagement of the proximal end of the jaw drive rod 4084 and the locking tab 4075. The jaw members 42, 44 may be manually opened and closed as needed in this fashion.

Figure 35A:
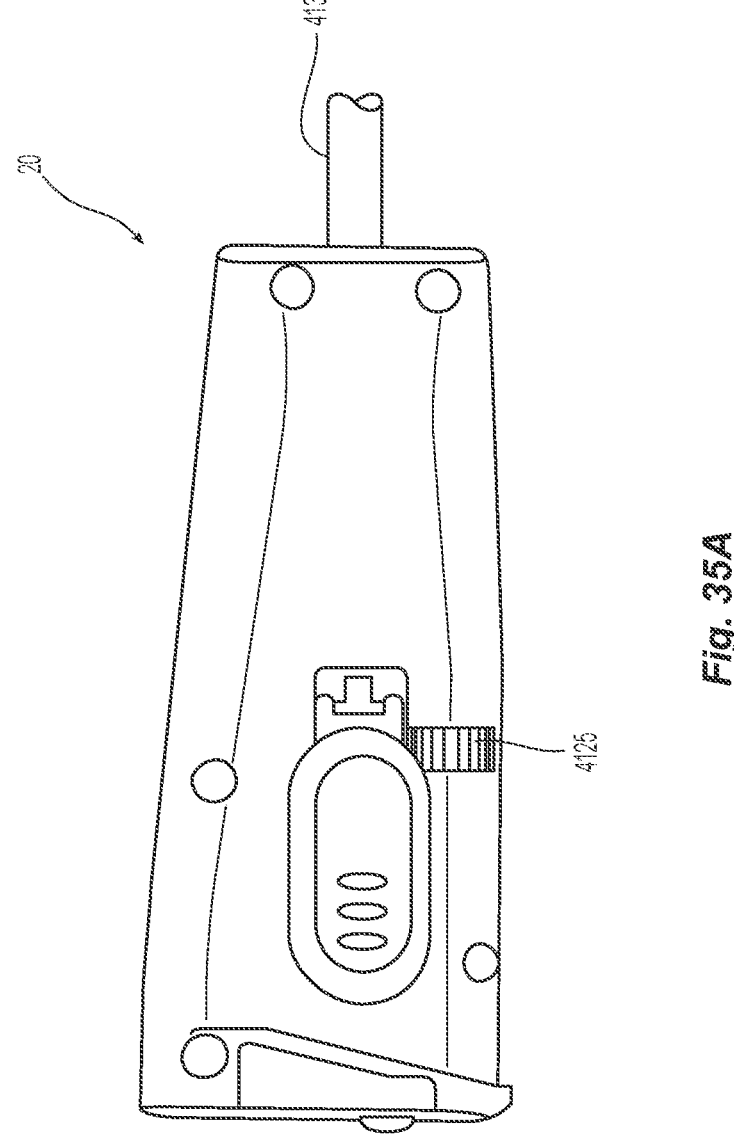
FIGS. 35A-35B show one embodiment of a manual jaw actuation assembly for use with the surgical instrument described herein including a thumb wheel accessible on an outside of the housing for exterior manipulation thereof.
Figure 35B:
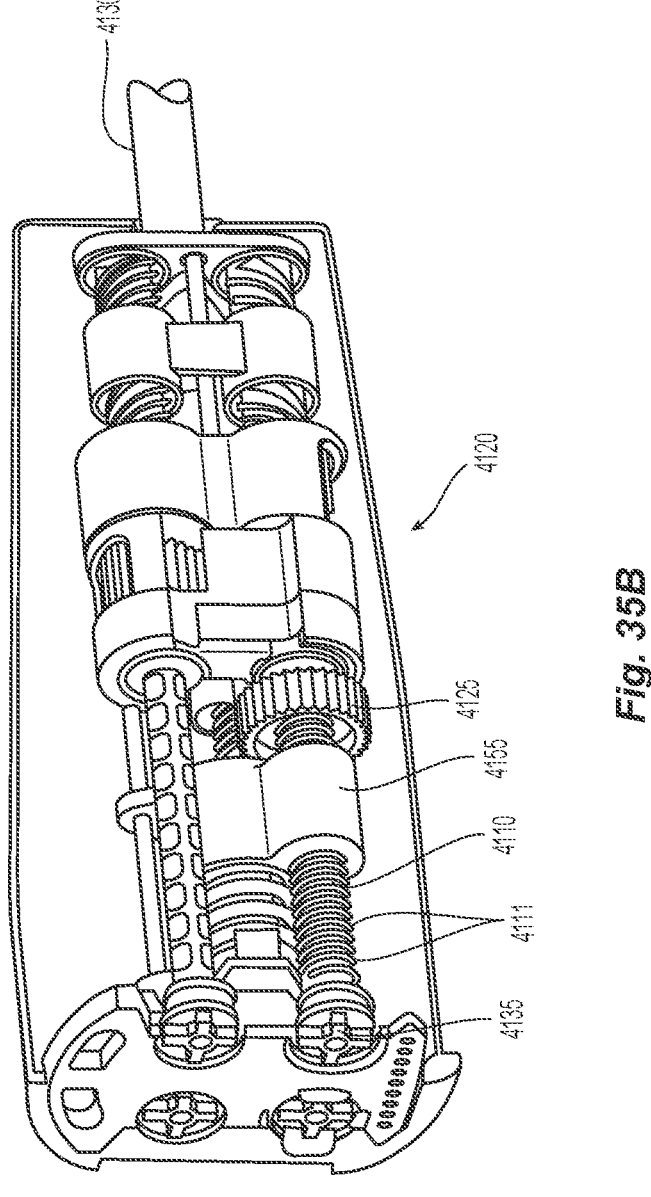

FIGS. 35A-35B are a side view and an internal perspective view, respectively, of one embodiment of a manual jaw actuation assembly 4120. In this embodiment, a thumb wheel 4125 is provided that extends through the jaw housing 20 for external access by an operator. The thumb wheel 4125 operably mates with the plurality of threads 4111 on the jaw input shaft 4110 distal to the spring compression assembly 4155. Rotation of the thumb wheel 4125 rotates the jaw input shaft 4110 which, in turn, translates the proximal hub (not shown but see FIG. 34 above) of the spring compression assembly 4155.

Figure 36A:
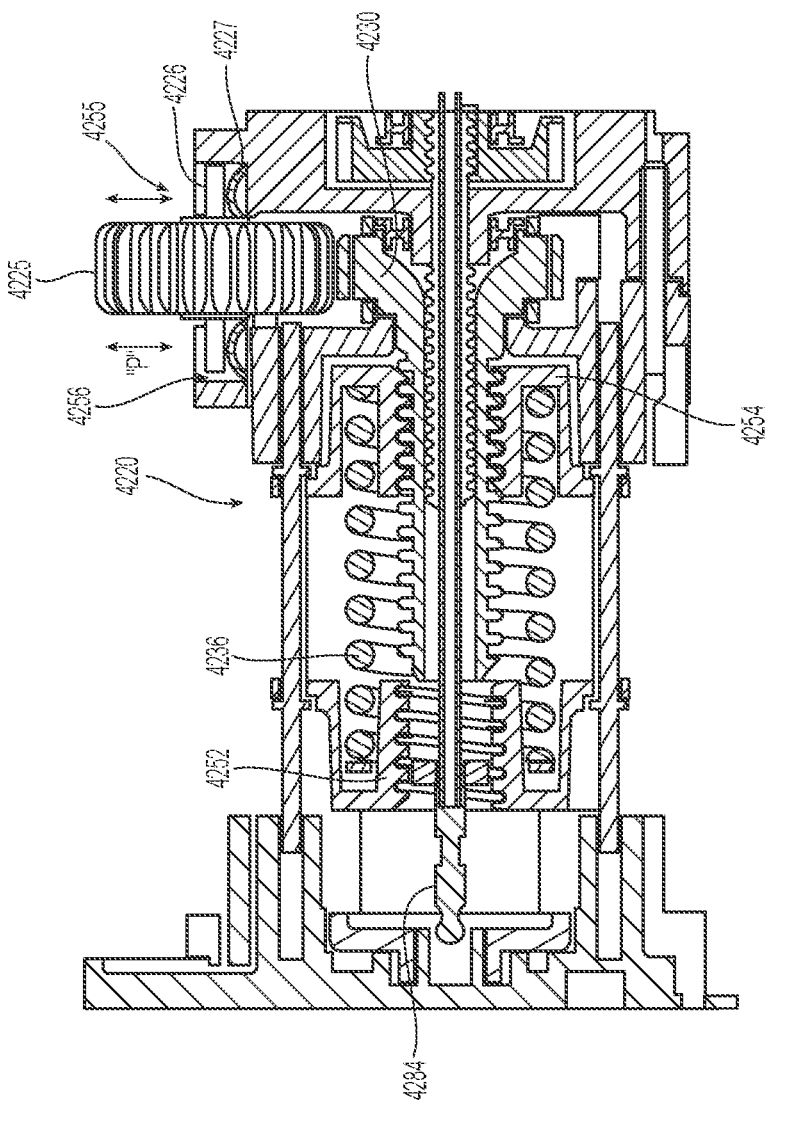
FIGS. 36A-36B show another embodiment of a manual jaw actuation assembly for use with the surgical instrument described herein including an exteriorly accessible thumb wheel configured to selectively engage a drive gear for actuating the end effector assembly.
Figure 36B:
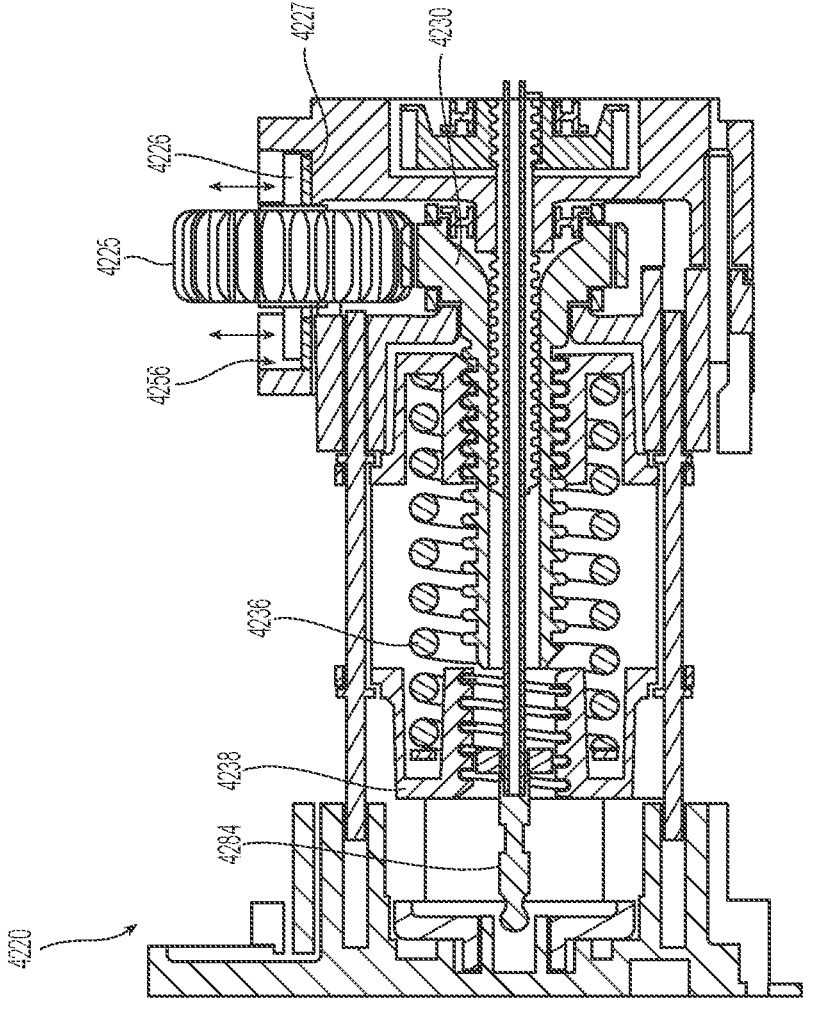
Figure 37A:
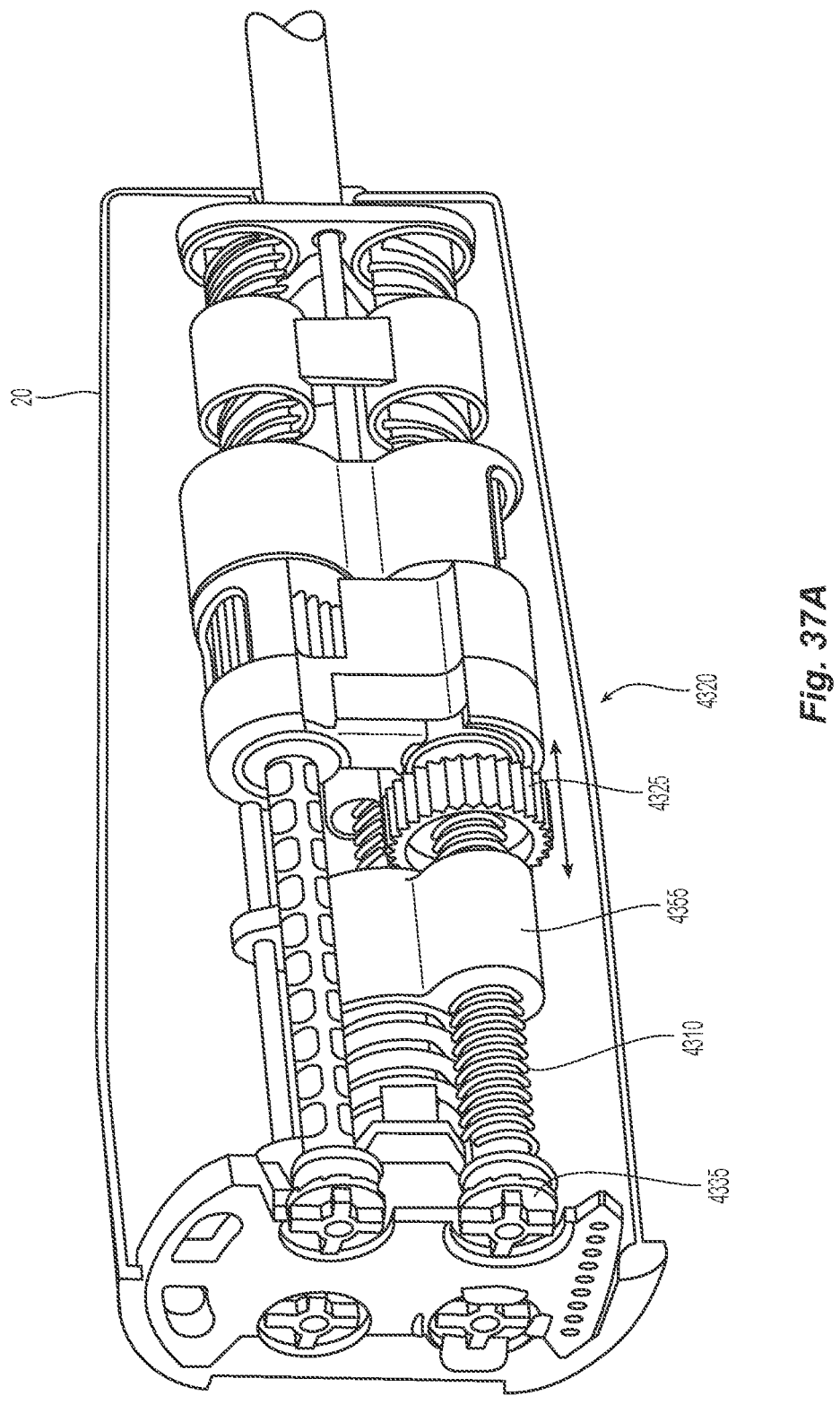
FIG. 37A-37E show another embodiment of a manual jaw actuation assembly for use with the surgical instrument described herein including an exteriorly accessible thumb wheel configured to selectively engage the drive gear for actuating the end effector assembly upon linear translation thereof.
Figure 37B:
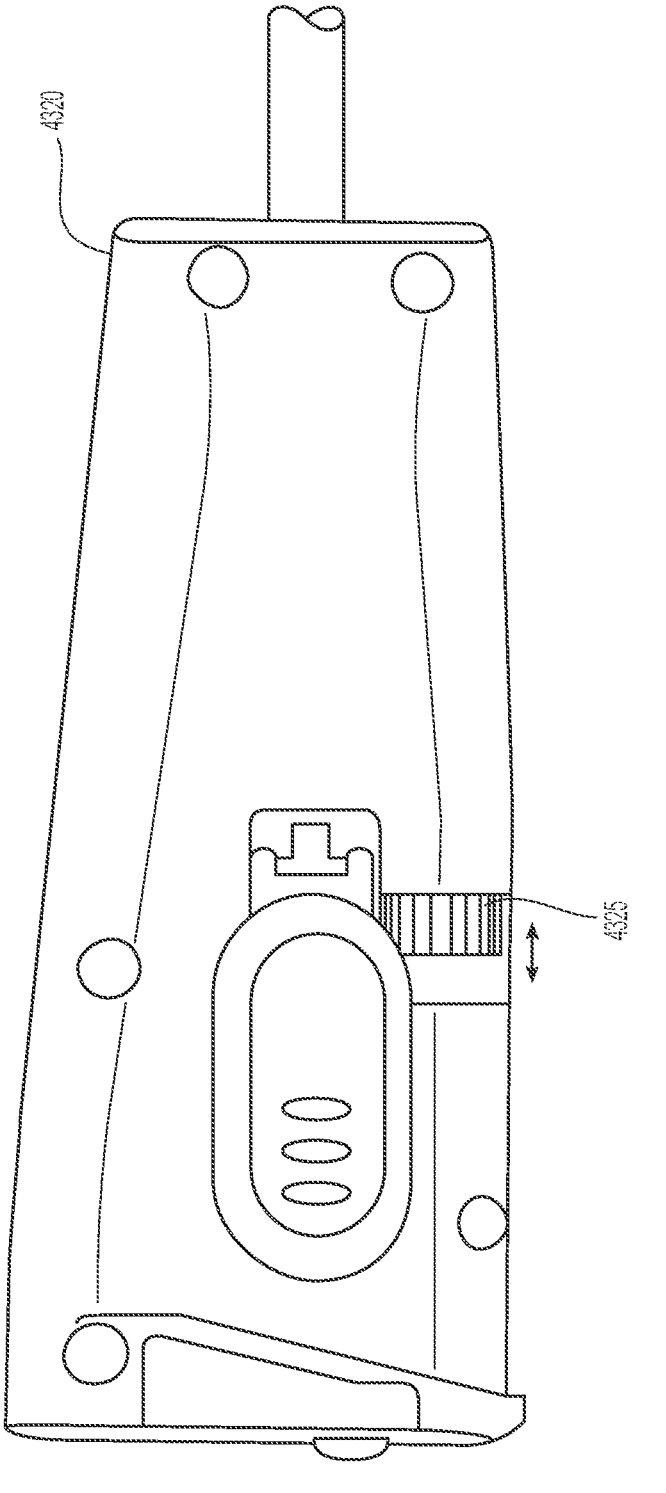
Figure 37C:
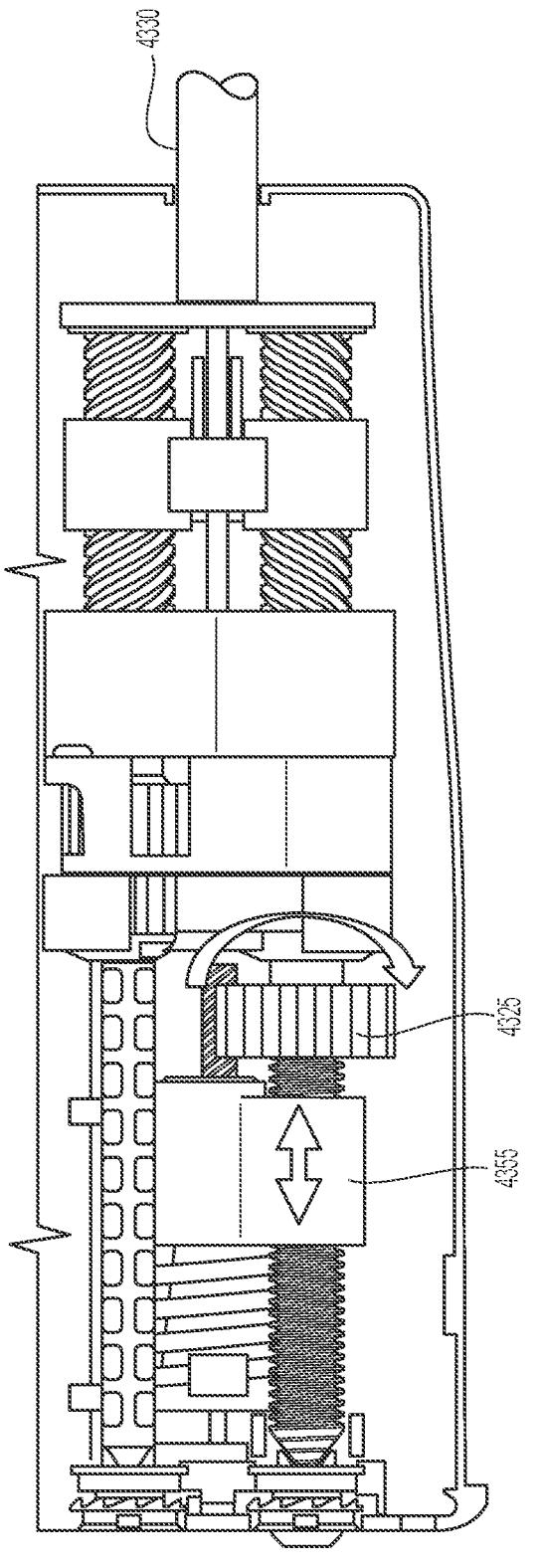
Figure 37E:
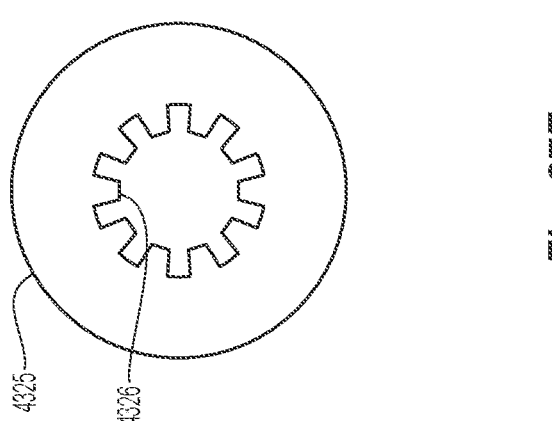
Figure 37D:
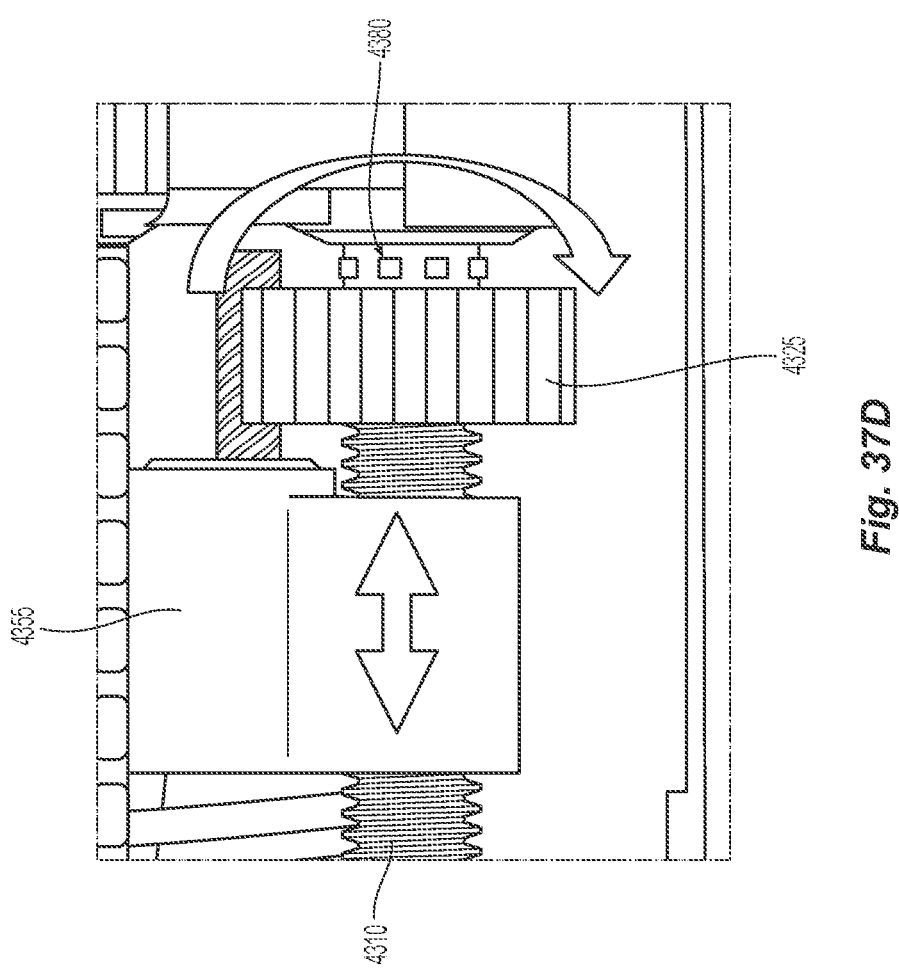

FIGS. 36A-36B are internal sides views of yet another embodiment of a manual jaw actuation assembly 4220. In this embodiment and similar to the previous embodiment, a thumb wheel 4225 is included and extends outside of the jaw housing 20 for external manual actuation. The thumb wheel 4225 is operably engageable with the spring compression assembly 4255 and is mounted thereto via a support axle 4226 that is configured to sit within a slot 4256 defined therein. More particularly, axle 4226 is supported within slot 4256 atop a leaf spring 4227 which is configured to bias the thumb wheel 4225 in a disengaged position. Thumb wheel 4225 is selectively moveable relative to the spring compression assembly 4255 (e.g., in the direction "P") between the disengaged position wherein the thumb wheel 4225 is spaced relative to the drive gear 4230 of the spring compression assembly 4255 (FIG. 36A) and an engaged position wherein the thumb wheel 4225 operably meshes with the drive gear 4230 to allow manual rotation of the drive gear 4230 to translate the proximal hub 4252 of the spring compression assembly 4255 relative to the distal hub 4254 of the spring compression assembly 4255 against the bias of the leaf spring 4227 (FIG. 36B). As noted above, translation of the jaw drive rod 4284 via translation of the proximal hub 4252 relative to the distal hub 4254 compresses spring 4236.

Manual rotation of the thumb wheel 4225 when disposed in the engaged position correspondingly translates the jaw drive rod 4284 to open and close the jaw members 42, 44. Upon release of the thumb wheel 4225, the thumb wheel 4225 disengages the drive gear 4230 under the bias of the leaf spring 4227 and returns to the disengaged position (FIG. 36B).

FIGS. 37A-37E are various views of yet another embodiment of a manual jaw actuation assembly 4320. In this embodiment and similar to the previous embodiments, a thumb wheel 4325 is included and extends outside of the jaw housing 20 for external manual actuation. The thumb wheel

4325 is operably engageable with the jaw input shaft 4310 of the jaw drive input 4335. More particularly, thumb wheel 4325 is positioned atop the jaw input shaft 4310 distal to the compression assembly 4355 and is laterally moveable thereon by the user to engage manual actuation. A spring (not shown) may be included to bias the thumb wheel 4325 in a disengaged position.

The jaw input shaft 4310 includes a series of castellations 4380 defined therein that are configured to matingly engage a corresponding series of teeth 4326 disposed on an inner peripheral surface of the thumb wheel 4325. The user pushes the thumb wheel 4325 distally to engage the castellations 4380 and the corresponding teeth 4326 and then rotates the thumb wheel 4325 to rotate the jaw input shaft 4310 and open or close the jaw members 42, 44. Other mechanical interfaces are also envisioned to accomplish this purpose. The user can manually engage and disengage the jaw input shaft 4310 as needed to actuate the jaw members 42, 44. If the thumb wheel 4325 is engaged under a spring bias, when the user releases the thumb wheel 4325, the thumb wheel 4325 automatically disengages from the jaw input shaft 4310 allowing unimpeded robotic actuation during surgery.

Figure 38B:
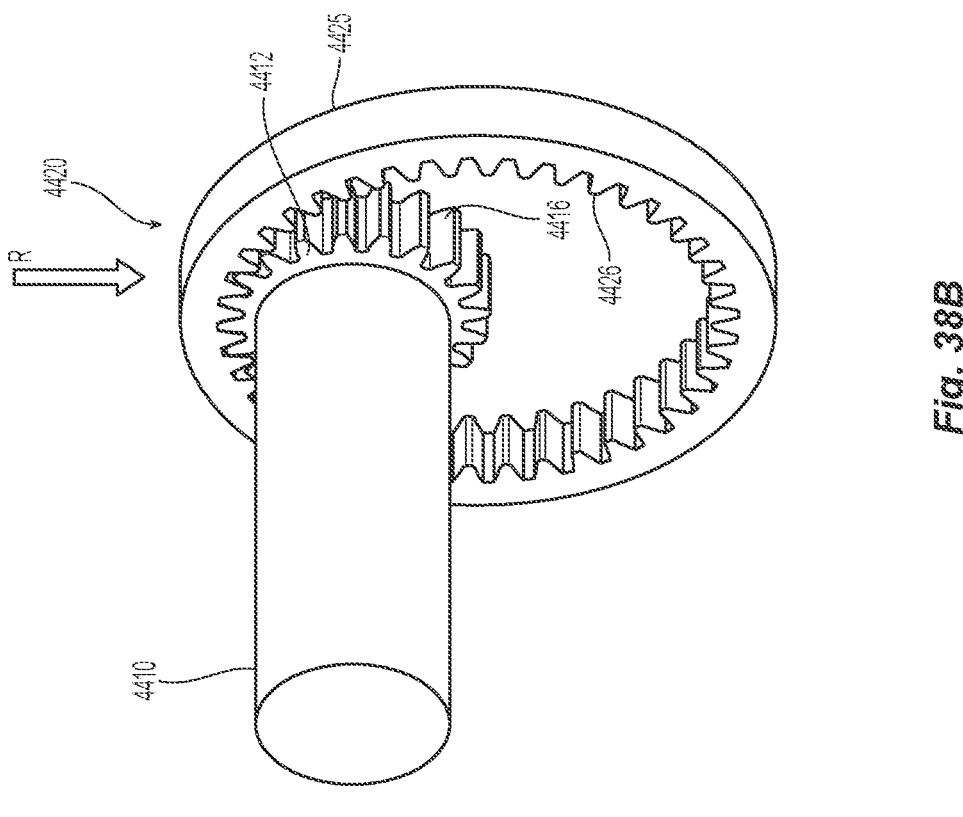
FIGS. 38A-38B show another embodiment of a manual jaw actuation assembly for use with the surgical instrument described herein including an exteriorly accessible thumb wheel configured to selectively engage a drive gear for actuating the end effector assembly upon radial movement thereof.
Figure 38A:
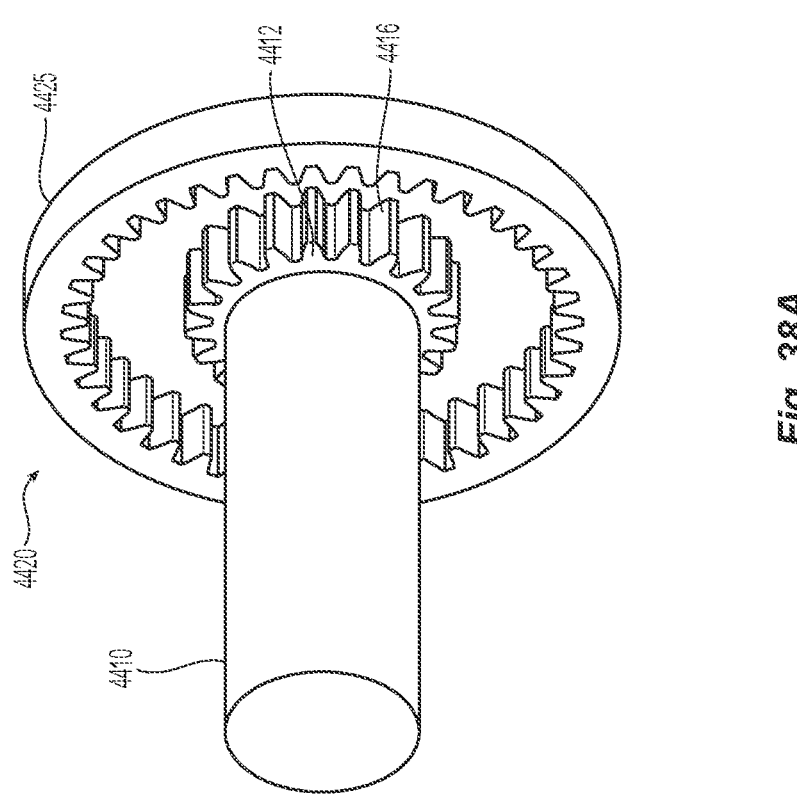

FIGS. 38A-38B are schematic views of yet another embodiment of a manual jaw actuation assembly 4420. In this embodiment and similar to the previous embodiments, a thumb wheel 4425 is included and extends outside of the jaw housing 20 for external manual actuation. Similar to the embodiment shown in FIGS. 37A-37E, the thumb wheel 4425 is manually engageable and disengageable with the jaw input shaft 4410. In this embodiment, the thumb wheel 4425 is radially movable to engage and disengage the jaw input shaft 4410 (See arrow "R").

More particularly, the thumb wheel 4425 includes a series of teeth 4426 disposed on an inner peripheral surface of the thumb wheel 4425 and the jaw input shaft 4410 includes a gear 4412 having series of corresponding teeth 4416 disposed on an outer periphery thereof. The user pushes the thumb wheel 4425 toward the jaw input shaft 4410 to engage the series of teeth 4416 of the gear 4412 with the corresponding teeth 4426 of the thumb wheel 4425 and then rotates the thumb wheel 4425 to rotate the jaw input shaft 4410 and open or close the jaw members 42, 44. The user can manually engage and disengage the jaw input shaft 4410 as needed to actuate the jaw members 42, 44. If the thumb wheel 4425 is engaged under a spring bias (spring not shown), when the user releases the thumb wheel 4425, the thumb wheel 4425 automatically disengages the from the jaw input shaft 4410 allowing unimpeded robotic actuation during surgery.

FIGS. 39A-39F show an embodiment of a selectively removable locking tab 4575 for use with the spring assembly 4550. More particularly, spring assembly 4550 includes, a compressor cap 4555 configured to receive a compression spring 4556 mounted atop a compressor stem 4545. The compressor stem 4545 includes an inner periphery 4547 defined therein configured to receive the jaw drive rod 4584 therethrough. A proximal end 4549 of the compressor stem 4545 includes an aperture 4551 defined therein configured in horizontal registration with the jaw drive rod 4584 for receipt therein. Proximal end 4549 also includes a vertical slot 4546 defined therein that extends passed aperture 4551 and that is configured to selectively receive the locking tab 4575 therein.

Locking tab 4575 includes a grasping tab 4577 that extends from an upper end thereof which is configured to be selectively graspable by the user to lock and unlock the jaw drive rod 4584 as needed during assembly and disassembly.

The locking tab 4575 includes a stem 4576 that extends from the grasping tab 4577 having a keyhole 4560 defined therein including an upper aperture 4579 and a lower, bigger aperture 4578. Locking tab 4575 is configured for receipt into slot 4546 in compressor stem 4545.

The proximal end 4585 of the jaw drive rod 4584 is key-like to include a first section 4588 at the proximal-most end thereof configured for receipt through aperture 4551 of compressor stem 4545 and second section 4586 sized larger than aperture 4551. A recess 4587 is defined between the first and second sections, 4588, 4586.

Figure 39A:
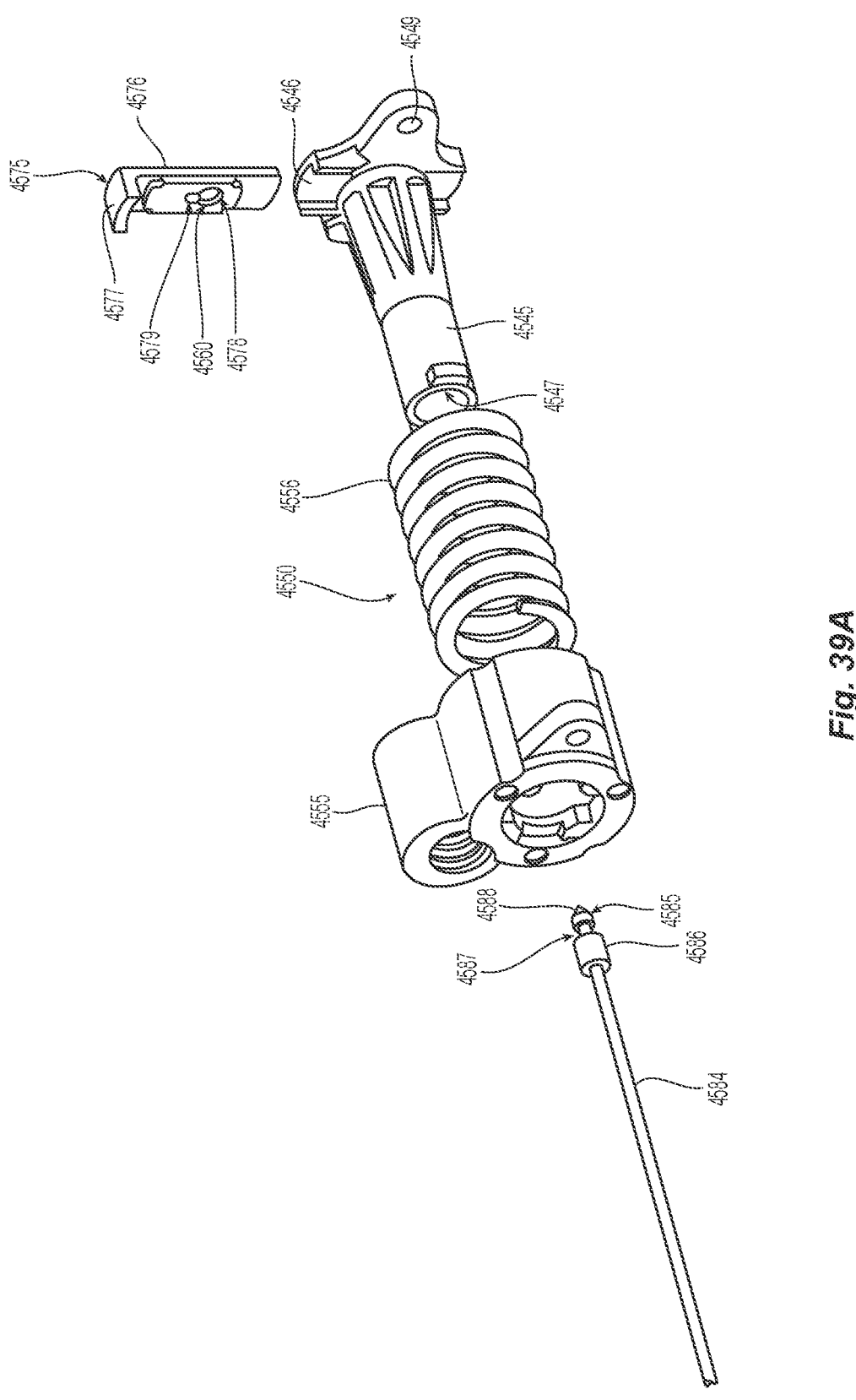
FIGS. 39A-39F show various views of a locking tab configured to releasably lock a drive rod that operably couples to the end effector assembly.
Figure 39B:
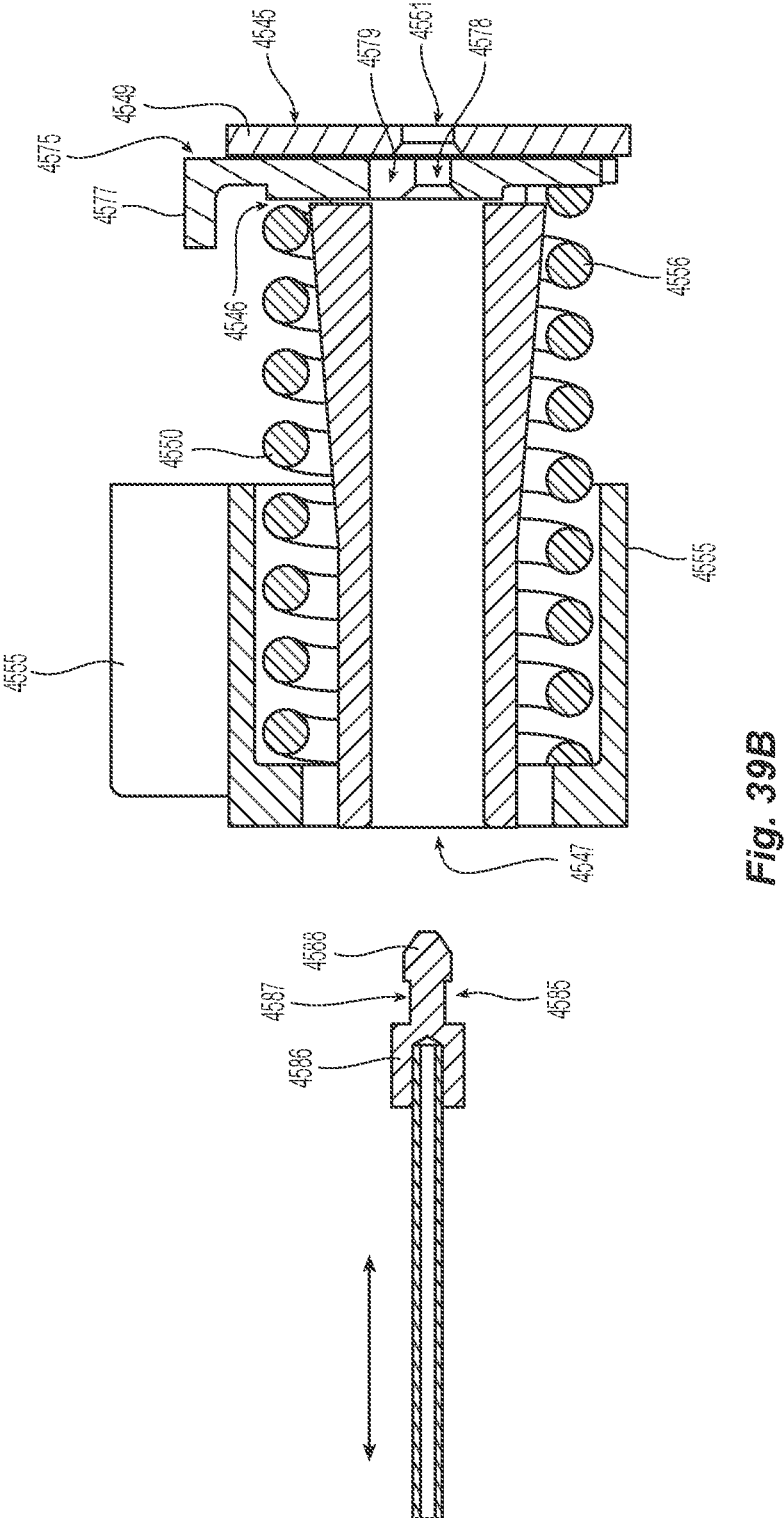
Figure 39D:
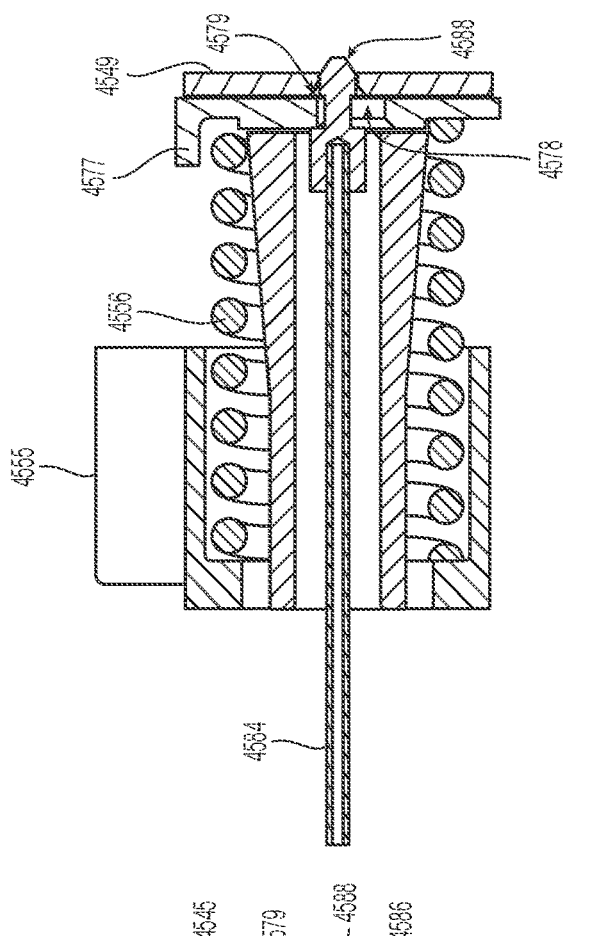
Figure 39C:
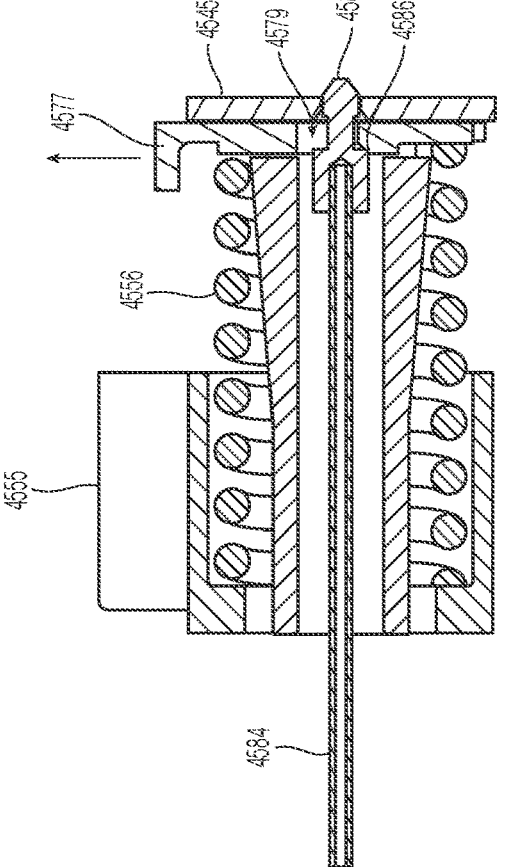
Figures 39E, 39F:
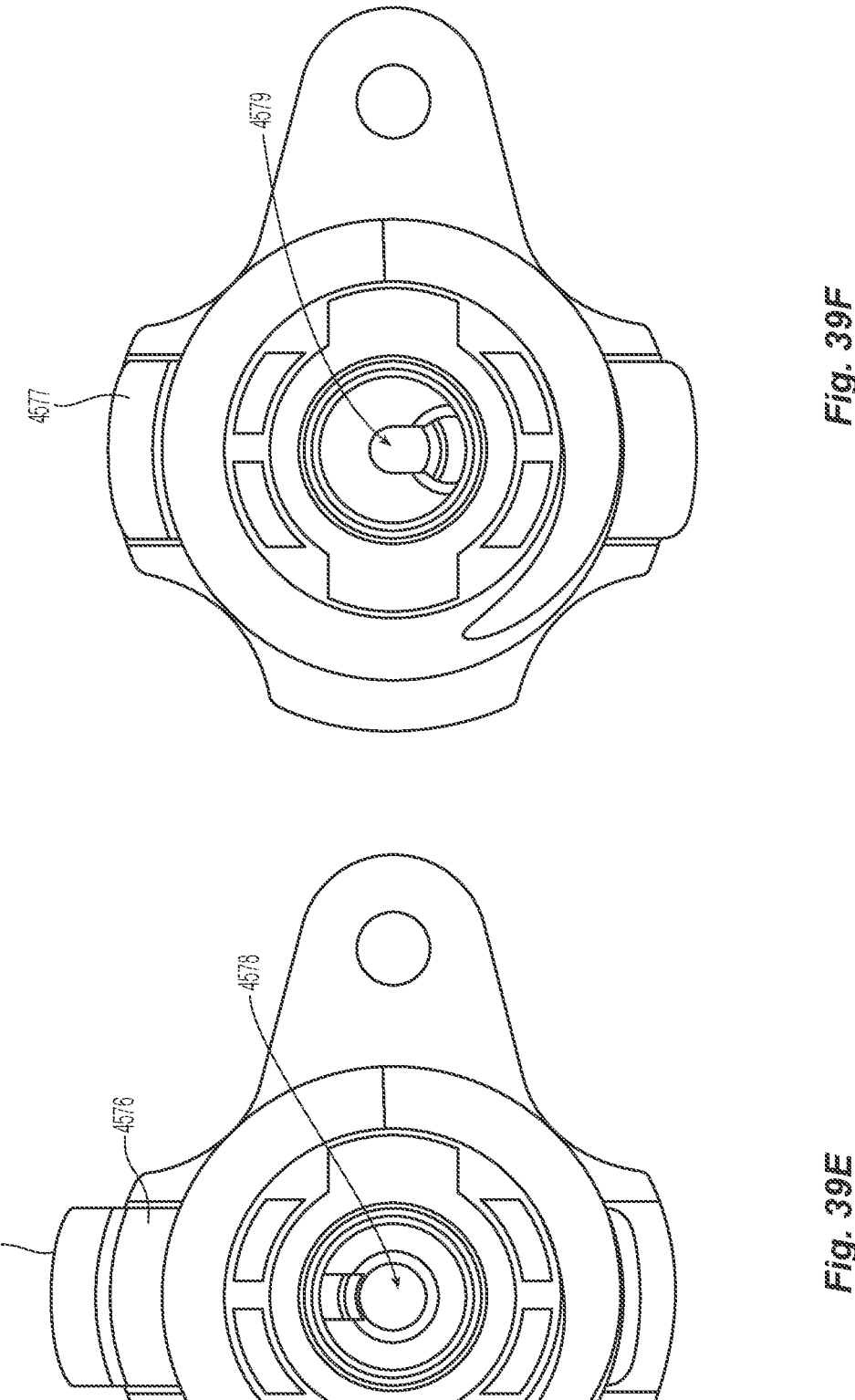

As shown in FIGS. 39B-39D, upon assembly, the compressor stem 4545, compressor spring 4550 and compressor cap 4555 are assembled and the locking tab 4575 is inserted into the slot 4546 of the compressor stem 4545 to a first loading position such that the lower aperture 4578 of the locking tab 4575 aligns with aperture 4551 of the compressor stem 4545. The proximal end 4585 of the jaw drive rod 4584 is then loaded into the inner periphery 4547 of the compressor stem 4545 such that the first section 4588 of the proximal end 4585 extends through aperture 4578 of the locking tab 4575 and through aperture 4551 of the compressor stem 4545. The second section is pushed into abutment with bigger aperture 4578. Once seated, the locking tab 4575 is pushed further into the compressor stem 4545 such that aperture 4579 slips into engagement atop the recess 4587 to lock the jaw drive rod 4584 in place for use (See FIG. 39F).

To disengage the jaw drive rod 4584, the user simply grasps the grasping tab 4577 and pulls the locking tab 4575 away from the housing 20. This disengages aperture 4579 from recess 4587 and aligns the first section 4588 with the aperture 4551 allowing removal of the jaw drive rod 4584 from the inner periphery 4547 of the compressor stem 4545 (See FIG. 39E).

Figure 40:
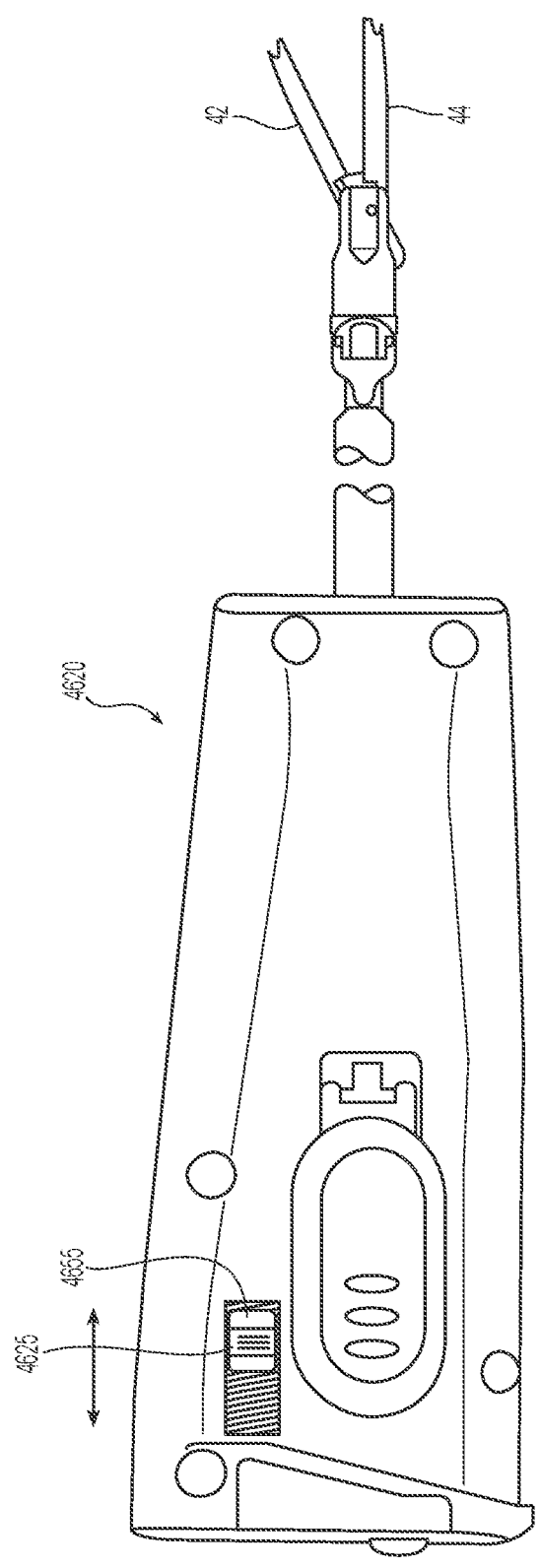
FIG. 40 shows another embodiment of a manual jaw actuation assembly for use with the surgical instrument described herein including an exteriorly accessible thumb wheel configured to selectively translate a spring compression assembly which, in turn, translates the drive gear to actuate the end effector assembly.

FIG. 40 is a side view of yet another embodiment of a manual jaw actuation assembly 4620. In this embodiment and similar to the previous embodiments, a thumb slide 4625 is included and is actuatable from the outside of jaw housing 20. The thumb slide 4625 is operably coupled to the spring compressor assembly 4655 such that sliding the thumb slide 4625 in either direction moves the spring compressor assembly 4655. More particularly, sliding the spring compressor assembly 4655 moves the distal hub relative to the proximal hub (e.g., distal and proximal hubs 4054, 4052 of FIG. 34) which, in turn, moves the jaw drive rod (e.g., jaw drive rod 4084 of FIG. 34) to open and close the jaw members 42, 44. A spring (not shown) may be employed to bias the slide in a particular direction.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended thereto.

What is claimed is:

1. A robotic surgical instrument, comprising:
a housing;
a shaft extending distally from the housing;
an end effector assembly disposed at a distal end portion of the shaft;
a jaw drive assembly disposed within the housing;

a drive rod extending distally from the housing through the shaft to the end effector assembly, the drive rod coupled between the jaw drive assembly and the end effector assembly such that actuation of the jaw drive assembly moves the drive rod relative to the shaft to actuate the end effector assembly, wherein the jaw drive assembly is adapted to connect to a surgical robot for driving the jaw drive assembly to thereby move the drive rod; and
a locking tab coupling the jaw drive assembly with the drive rod within the housing, the locking tab received within a slot of the jaw drive assembly and configured to enable manual manipulation of the locking tab from an engaged position, wherein the locking tab moves within the slot such that a keyhole of the locking tab engages a key of the drive rod to maintain the coupling of the jaw drive assembly with the drive rod, to a disengaged position, wherein the locking tab moves within the slot such that the keyhole of the locking tab is disengaged from the key of the drive rod to disengage the jaw drive assembly from the drive rod, thereby enabling selective engagement of the end effector assembly with the jaw drive assembly.

2. The robotic surgical instrument according to claim 1, further comprising a spring assembly coupling the drive rod with the jaw drive assembly.

3. The robotic surgical instrument according to claim 2, wherein the spring assembly includes a first hub coupled to a drive input shaft of the jaw drive assembly, a second hub coupled to the drive rod, and a spring disposed between the first and second hubs.

4. The robotic surgical instrument according to claim 3, wherein, in the engaged position of the locking tab, the drive rod is coupled to the second hub of the spring assembly and wherein, in the disengaged position of the locking tab, the drive rod is disengaged from the second hub of the spring assembly.

5. The robotic surgical instrument according to claim 3, wherein the spring is configured to regulate a force applied from the first hub to the second hub.

6. The robotic surgical instrument according to claim 3, wherein the second hub includes the slot of the drive assembly, and the locking tab is received within the slot in the second hub.

7. The robotic surgical instrument according to claim 1, wherein the locking tab is movable within the slot from the engaged position to the disengaged position.

8. The robotic surgical instrument according to claim 1, wherein the end effector assembly includes first and second jaw members and wherein the actuation of the end effector assembly includes movement of at least one of the first or second jaw members relative to the other of the first or second jaw members.

9. The robotic surgical instrument according to claim 8, wherein at least one of the first or second jaw members is adapted to connect to a source of energy for conducting energy through tissue grasped between the first and second jaw members.

10. The robotic surgical instrument according to claim 1, wherein the shaft includes an articulating portion configured to articulate the end effector assembly relative to the housing.

* * * * *